(12) United States Patent
Freese et al.

(10) Patent No.: US 12,191,010 B2
(45) Date of Patent: Jan. 7, 2025

(54) SYSTEMS AND METHODS FOR MACHINE LEARNING BASED ERROR CORRECTION IN LARGE DATA STRUCTURES

(71) Applicant: STChealth, LLC, Phoenix, AZ (US)

(72) Inventors: Kyle Freese, Scottsdale, AZ (US); Sawyer Koops, Phoenix, AZ (US); Nate Meckes, Durham, NC (US)

(73) Assignee: STChealth, LLC

( * ) Notice: Subject to any disclaimer, the term of this patent is extended or adjusted under 35 U.S.C. 154(b) by 23 days.

(21) Appl. No.: 18/104,195

(22) Filed: Jan. 31, 2023

(65) Prior Publication Data
US 2024/0257927 A1    Aug. 1, 2024

(51) Int. Cl.
*G06F 16/215*    (2019.01)
*G16H 10/60*    (2018.01)

(52) U.S. Cl.
CPC .......... *G16H 10/60* (2018.01); *G06F 16/215* (2019.01)

(58) Field of Classification Search
CPC .............................. G06F 16/215; G16H 10/60
See application file for complete search history.

(56) References Cited

U.S. PATENT DOCUMENTS

| | | | |
|---|---|---|---|
| 10,229,186 B1 * | 3/2019 | Reiner | G06F 16/334 |
| 2015/0088545 A1 * | 3/2015 | Daub | H04W 4/60 |
| | | | 705/3 |
| 2017/0208041 A1 * | 7/2017 | Kho | G16H 10/60 |
| 2018/0025093 A1 * | 1/2018 | Xia | G06F 16/9024 |
| | | | 707/602 |
| 2021/0374890 A1 * | 12/2021 | Lu | G06Q 30/0185 |
| 2023/0023440 A1 * | 1/2023 | Casey | G16H 50/50 |
| 2023/0088474 A1 * | 3/2023 | Sragow | G16H 10/60 |
| | | | 705/2 |
| 2024/0037197 A1 * | 2/2024 | Yarabolu | G06F 21/6218 |
| 2024/0065767 A1 * | 2/2024 | Cordonnier | A61F 2/4611 |

* cited by examiner

*Primary Examiner* — Tarek Chbouki
(74) *Attorney, Agent, or Firm* — SNELL & WILMER L.L.P.

(57) ABSTRACT

A consumer health records access platform includes a software application for operation on a user device, the system comprising a processor, a tangible, non-transitory electronic memory in electronic communication with the processor a set of computer readable code on the non-transitory electronic memory, including a consumer module configured for use by consumers to support registering consumers for a consumer account pending authentication and approval by a healthcare provider, a provider module configured to enable, via a healthcare provider account, the healthcare provider to look up the consumer account pending authentication and to authenticate and approve or reject creation of the consumer account, a recording agency module configured for use by recording agency representatives to create, via a recording agency account, the healthcare provider account, a consumer health record access database comprising a plurality health records associated on a many to one basis with each of a plurality of consumer accounts.

27 Claims, 19 Drawing Sheets

≡  MyIR Mobile

— Register —

Check your personal information below.

Name:            Jane Doe
Gender:          Female
Date of birth:   July 5, 1970
Phone number:    (555)555-555
Address:         321 W. Lorem Ipsum Ct.
                 Anytown, USA

*By creating an account you agree to our Terms of Service and Privacy Policy

Continue  602

Update your information  604

```
┌─────────────────────────────────────────────────────────────┐
│ Store a similarity threshold value, a dissimiality threshold │
│ value and a training data set of health records (1202)      │
└─────────────────────────────────────────────────────────────┘
                              │
┌─────────────────────────────────────────────────────────────┐
│            Execute a data processing module (1204)          │
└─────────────────────────────────────────────────────────────┘
                              │
┌─────────────────────────────────────────────────────────────┐
│  Calculate a first set of weights associated with a first    │
│                   set of factors (1006)                      │
└─────────────────────────────────────────────────────────────┘
                              │
┌─────────────────────────────────────────────────────────────┐
│  Enter the weights and factors into a similarity score       │
│                       model (1208)                           │
└─────────────────────────────────────────────────────────────┘
                              │
┌─────────────────────────────────────────────────────────────┐
│         Execute the similarity score module (1210)          │
└─────────────────────────────────────────────────────────────┘
                              │
┌─────────────────────────────────────────────────────────────┐
│ Compare the similarity score to the relevant threshold value │
│ and determine a subset of health records based on relevant   │
│                       value (1212)                           │
└─────────────────────────────────────────────────────────────┘
                              │
┌─────────────────────────────────────────────────────────────┐
│ Flag health records as similar or dissimilar based on        │
│           comparing the similarity score (1214)              │
└─────────────────────────────────────────────────────────────┘
                              │
┌─────────────────────────────────────────────────────────────┐
│  Execute a corrective action based on the flagged records    │
│                          (1216)                              │
└─────────────────────────────────────────────────────────────┘
```

FIG.12

SYSTEMS AND METHODS FOR MACHINE LEARNING BASED ERROR CORRECTION IN LARGE DATA STRUCTURES

TECHNICAL FIELD

The present disclosure generally relates to database management, and more particularly, to systems that reconcile and integrate information from multiple separated databases, for example government-controlled databases located in different states.

BACKGROUND

Current health records technologies suffer from gaps in the healthcare software space. For example, after an immunization is given, the administering agent (typically a pharmacy, hospital, doctor's office, or other health care facility) is often responsible for submitting records of the immunization to a recording agency—typically a state and/or federal body with statutory authority to maintain these records. As a result, immunization records for a particular individual may be fragmented among various entities, databases, and so forth. Accordingly, it may be difficult and/or impossible to determine a comprehensive immunization status for a particular individual. Furthermore, such ad-hoc and fragment reporting may tend to introduce errors between databases. Accordingly, improved systems and methods for accessing, grouping, utilizing, reporting, validating and/or otherwise managing health records, for example immunization records, are desirable.

SUMMARY

In various embodiments a consumer health records access platform includes a software application for operation on a user device, the system comprising a processor, a tangible, non-transitory electronic memory in electronic communication with the processor a set of computer readable code on the non-transitory electronic memory, including a consumer module configured for use by consumers to support registering consumers for a consumer account pending authentication and approval by a healthcare provider, a provider module configured to enable, via a healthcare provider account, the healthcare provider to look up the consumer account pending authentication and to authenticate and approve or reject creation of the consumer account, a recording agency module configured for use by recording agency representatives to create, via a recording agency account, the healthcare provider account, a consumer health record access database comprising a plurality health records associated on a many to one basis with each of a plurality of consumer accounts, a training data set of health records, a plurality of factors stored in association with each health record associated with the respective consumer account, a data processing module, executable by the processor, configured to apply algorithmic transformations to the health records and comprising a machine learning module including a self learning system, a training system, and a feedback system, wherein, in response to execution by the processor, the self learning system automatically calculates a first set of weights associated with a first set of factors of a plurality of factors, stored in association with each health record of the training data set of health records, and enters the first set of weights and first set of associated factors into a similarity score model, a similarity threshold value, a dissimilarity threshold value, a factor entering module, executable by the processor, to enter at least one factor from the plurality of factors stored in association with each health record associated with the respective consumer account into a similarity score module, wherein the similarity score module is executable by the processor to calculate a similarity score for each one of the plurality of health records associated with the respective customer account, wherein the respective similarity score for the respective health record is based on at least one weight of the first set of weights and at least one factor of the first set of factors of the similarity score model, a comparator that is executable by the processor to compare the similarity score for each record with the similarity threshold value and the dissimilarity threshold value to determine a subset of the health records which exceed either value, a flagging unit that is executable by the processor to flag health records as similar or as dissimilar based on the output of the comparator, and a corrective action module that is executable by the processor to perform a corrective action only for those consumer accounts which have associated health records flagged by the flagging unit.

In various embodiments, the feedback system is executable by the processor, to automatically update at least one weight of the first set of weights associated with the first set of factors of the plurality of factors stored in association with each health record associated with the respective consumer account based on information received by the feedback system, wherein the self learning system is executable to generate a second set of weights including the updated weight for entry into the similarity score model, wherein the similarity score module calculates a different similarity score for a selected heath record before the feedback system is executed than after. In various embodiments, the feedback system is executable by the processor to automatically remove at least one factor of the first set of factors in response to information received by the feedback system. In various embodiments, the feedback system is executable by the processor to automatically add at least one factor to the first set of factors in response to information received by the feedback system, wherein the self learning system is executable to generate a second set of factors including the added factor for entry into the similarity score model.

In various embodiments, at least one of the factors entered into the similarity score model is a first name. In various embodiments, at least one of the factors entered into the similarity score model is a last name. In various embodiments, at least one of the factors entered into the similarity score model is a date of birth. In various embodiments, at least one of the factors entered into the similarity score model is a social security number or taxpayer ID number. In various embodiments, at least one of the factors entered into the similarity score model is a year of birth. In various embodiments, at least one of the factors entered into the similarity score model is a gender. In various embodiments, at least one of the factors entered into the similarity score model is a birth order. In various embodiments, at least one of the factors entered into the similarity score model is a street address. In various embodiments, at least one of the factors entered into the similarity score model is a zip code. In various embodiments, at least one of the factors entered into the similarity score model is the output of a hash function.

In various embodiments, the hash function is based on record elements comprising at least one of a first name, a last name, a date of birth, a first name character length, a last name character length, a combined first and last name character length, a date of birth year, a first name initial, or a last name initial. In various embodiments, the hash function returns an eight digit integer. In various embodiments, the corrective action module allows for in response to receiving user input identifying flagged health records as similar, entering information into the feedback system confirming the health records as similar, and responsively merging the health records. In various embodiments, the corrective action module allows for in response to receiving user input identifying flagged health records as dissimilar, entering information into the feedback system confirming the health records as dissimilar, and responsively storing the dissimilar health records in the consumer health record access database as new health records. In various embodiments, the comparator allows for comparing the similarity score for each health record of a set of incoming health records received via bi-directional HL7 messaging from each of the healthcare provider and a state immunization registry to the similarity score for each of the plurality of health records of the consumer health record access database.

The contents of this summary section are provided only as a simplified introduction to the disclosure, and are not intended to be used to limit the scope of the appended claims.

BRIEF DESCRIPTION OF THE DRAWINGS

With reference to the following description, appended claims, and accompanying drawings:

FIG. 2F illustrates an exemplary immunization and forecasting report of an exemplary consumer health record access system in accordance with various embodiments;

FIG. 6 illustrates a confirmation page of an exemplary consumer health record access system in accordance with various embodiments;

FIG. 12 illustrates a corrective action process in an exemplary consumer health record access system in accordance with various embodiments.

DETAILED DESCRIPTION

Figure 1:
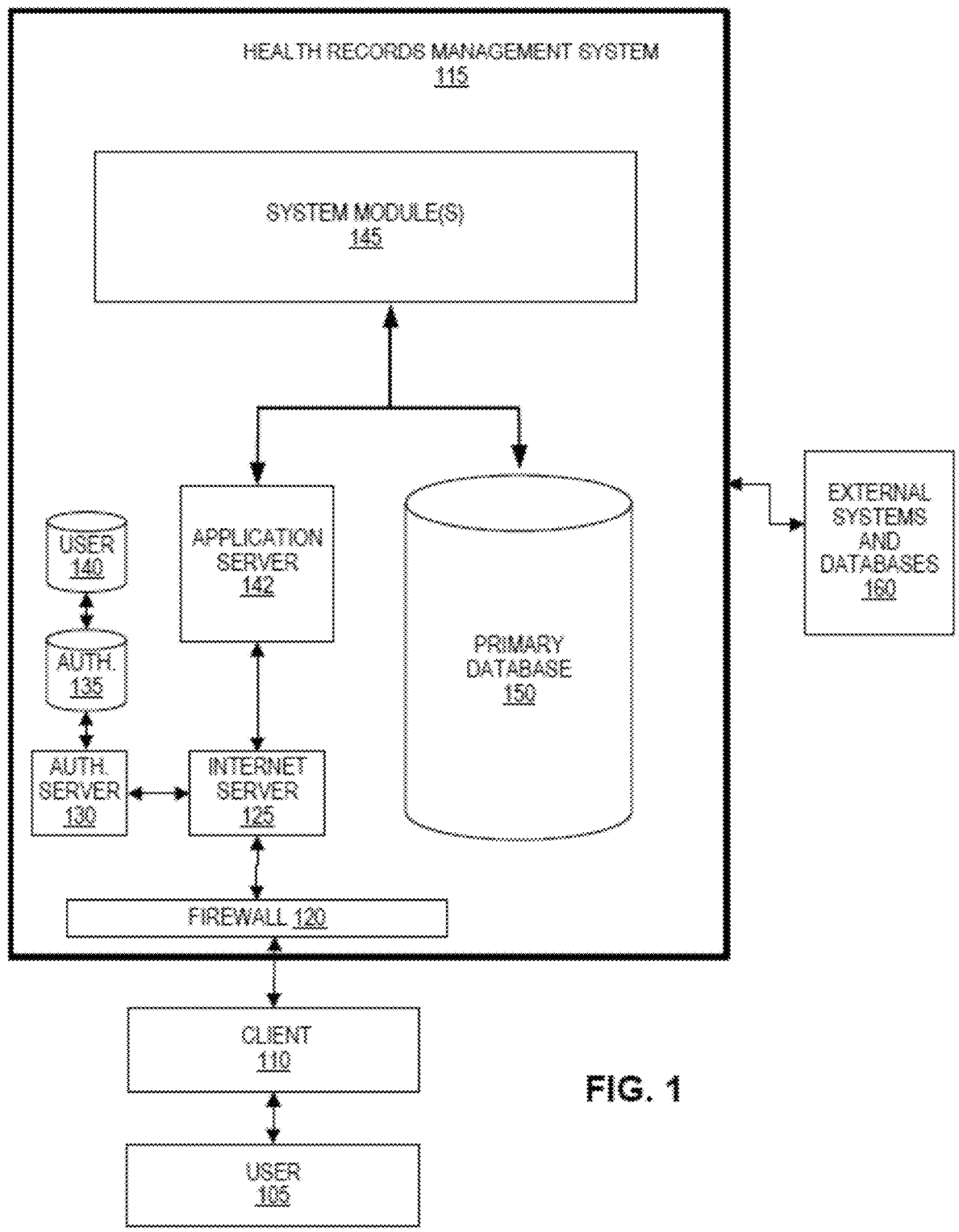
FIG. 1 is a block diagram illustrating exemplary health records management system components, in accordance with various embodiments.

The following description is of various embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure or appended claims.

It should be appreciated that exemplary components and steps may be realized by any number of hardware, software, or other components configured to perform the specified functions. For example, an exemplary embodiment employs various graphical user interfaces, software components, and networking and/or database functionality. In addition, various embodiments may be practiced in any number of medical record management and/or information management contexts, and the embodiments disclosed are merely indicative of exemplary applications. For example, the principles, features and methods discussed may be applied to various industries, and are not limited to use in connection with health records and/or immunizations.

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and/or functional changes may be made without departing from the spirit and scope of the disclosure. Thus, the detailed description herein is presented for purposes of illustration only and not of limitation. For example, the steps recited in any of the method or process descriptions may be executed in various orders and are not limited to the order presented. Moreover, certain of the functions or steps may be outsourced to or performed by one or more third parties. Furthermore, any reference to singular includes plural embodiments, and any reference to more than one component may include a singular embodiment.

Systems, methods and computer program products are provided. In the detailed description herein, references to "an exemplary embodiment", "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "match" or "associated with" or similar phrases may include an identical match, a partial match, meeting certain criteria, matching a subset of data, a correlation, satisfying certain criteria, a correspondence, an association, an algorithmic relationship and/or the like. Similarly, as used herein, "authenticate" or similar terms may include an exact authentication, a partial authentication, authenticating a subset of data, a correspondence, satisfying certain criteria, an association, an algorithmic relationship and/or the like.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional techniques for data networking, software application development, cloud computing, and/or the like, may not be described in detail herein. Furthermore, the connecting lines shown in various figures contained herein are intended to represent exemplary functional relationships and/or physical or communicative couplings between various elements. It should be noted that many alternative or additional functional relationships or physical or communicative connections may be present in a practical health records management system.

In response to the growing awareness of pandemic risk, there is increased pressure for entities performing immunizations (i.e. the "reporting agency") and entities recording immunizations (i.e. the "recording agency") to meet government data reporting and recording guidelines in an aggressive and timely manner. Existing software based immunization reporting systems struggle to meet this technical challenge. In particular, recording agencies dealing with large data sets (such as, for example, a State Immunization Information System (IIS)) must have a mechanism for identifying individuals.

There are many sorts of existing identification schemas, but they tend to be unique to individuals or reporting agencies. As a result, recording agencies may tend to receive multiple data records for the same individual. In this regard, existing systems for recording agencies introduce a technical challenge of processing large numbers of potentially duplicate records. Processing multiple duplicate records tends to reduce processing efficiency, storage efficiency, and search efficiency while increasing system energy consumption and capital expenditure (i.e., increased hardware cost for additional storage and processing capacity). The systems and methods described herein provide a technical solution by enabling enhanced data deduplication. For the purposes of deduplication, existing individual ID numbers tend not to be particularly useful when applying traditional techniques for deduplication because incoming/external records do not share those same IDs. The systems and processes herein improve traditional systems by providing a technical solution to find, process, and eliminate duplicate records. In this regard, the systems and methods disclosed herein provide technical improvements over traditional systems by increasing processing efficiency, increasing storage efficiency, reducing processor overhead, and accelerating search speeds even where reporting agency records comprise multiple IDs associated with the same underlying individual.

With reference now to FIG. 1, in various exemplary embodiments a health records management system, for example system 115, is configured to provide vaccine administration records functionality, reminders, vaccination reports, vaccine inventory levels, demand forecasts, and the like. A health records management system may be any system configured to facilitate storage and/or transmission of health records information, for example information regarding immunizations.

In general, system 115 may comprise any systems, components, and/or modules (e.g., system modules 145) configured with any suitable methods, algorithms, and/or techniques for health records management. Additionally, system 115 may also suitably interface with any number and/or type of external systems 160, for example client computers, medical provider computers, government computers and the like, for example via a common network such as the Internet.

Principles of the present disclosure contemplate improved health records management methods and systems. By providing a centralized repository for health records, system users can achieve faster and simpler access to immunization information, immunization reminders, family member evaluations, and so forth. Moreover, systems and methods configured in accordance with principles of the present disclosure may tend to result in improved public health outcomes, for example increased immunization levels or increased reliability of immunization data associated with individual populations (e.g., by deduplication of the associated records).

In various exemplary embodiments, according to principles of the present disclosure, systems and methods are configured to provide conditioned access to public health records, for example immunization records. As opposed to conventional medical records systems that leverage the electronic medical records of a clinical healthcare provider, systems and methods of the present disclosure leverage a central population public health data system (for example, one or more state immunization registries).

In various embodiments, exemplary health records management systems include a user interface ("UI"), software modules, logic engines, various databases, interfaces to systems and tools, and/or computer networks. While exemplary health records management systems may contemplate upgrades or reconfigurations of existing processes and/or systems, changes to existing databases and system tools are not necessarily required by principles of the present disclosure.

As used herein, an "entity" may include any individual, software program, business, organization, government entity, web site, system, hardware, and/or any other entity. A "user" may include any entity that interacts with a system and/or participates in a process. In various exemplary embodiments, a user is one or more of a consumer, a healthcare provider, or a representative of a state immunization registry.

Continuing to reference FIG. 1, in accordance with various embodiments, a user 105 may perform tasks such as requesting, retrieving, receiving, updating, analyzing and/or modifying data. User 105 may also perform tasks such as initiating, manipulating, interacting with or using a software application, tool, module or hardware, and initiating, receiving or sending a communication. User 105 may interface with Internet server 125 via any communication protocol, user device or method discussed herein, known in the art, or later developed. User 105 may be, for example, a patient, a medical provider, a state records administrator, a health records provider, and/or the like. In various embodiments, a user device may comprise software and/or hardware in communication with the system via a network comprising hardware and/or software configured to allow a transaction account owner, a user, and/or the like, access to the health records system 115. The user device may comprise any suitable device that is configured to allow a user to communicate with a network and the health records system 115. The user device may include, for example, a personal computer, personal digital assistant, cellular phone, tablet, kiosk, and/or the like and may allow a user to transmit biometric information, voice communications, and/or the like.

In various embodiments, a health records management system 115 may provide access to a user 105 interfacing with system 115 by way of a client 110. Health records management system 115 may be a partially or fully integrated system comprised of various subsystems, modules and databases. Client 110 comprises any hardware and/or software suitably configured to facilitate entering, accessing, requesting, retrieving, updating, analyzing, and/or modifying data. The data may include health records (e.g., patient information, provider information, medical procedure information, clinical information, diagnostic information, immunization records, prescription information, family information, genetic information, and/or the like), or any other suitable information discussed herein.

Client 110 includes any device (e.g., a computer), which communicates, in any manner discussed herein, with health records management system 115 via any network or protocol discussed herein. Browser applications comprise Internet browsing software installed within a computing unit or system to conduct online communications and transactions. These computing units or systems may take the form of personal computers, mobile phones, personal digital assistants, mobile email devices, laptops, notebooks, hand-held computers, portable computers, tablets, kiosks, and/or the like. Practitioners will appreciate that client 110 may or may not be in direct contact with health records management system 115. For example, client 110 may access the services of health records management system 115 through another server, which may have a direct or indirect connection to Internet server 125. Practitioners will further recognize that client 110 may present interfaces associated with a software application or module that are provided to client 110 via application graphical user interfaces (GUIs) or other interfaces and are not necessarily associated with or dependent upon Internet browsers or internet specific protocols.

User 105 may communicate with health records management system 115 through a firewall 120, for example to help ensure the integrity of health records management system 115 components. Internet server 125 may include any hardware and/or software suitably configured to facilitate communications between the client 110 and one or more health records management system 115 components.

Firewall 120, as used herein, may comprise any hardware and/or software suitably configured to protect health records management system 115 components from users of other networks. Firewall 120 may reside in varying configurations including stateful inspection, proxy based and packet filtering, among others. Firewall 120 may be integrated as software within Internet server 125, or another system 115 component, or may reside within another computing device or may take the form of a standalone hardware component.

Authentication server 130 may include any hardware and/or software suitably configured to receive authentication credentials, encrypt and decrypt credentials, authenticate credentials, and/or grant access rights according to predefined privileges associated with the credentials. Authentication server 130 may grant varying degrees of application and/or data level access to users based on information stored within authentication database 135 and user database 140. Application server 142 may include any hardware and/or software suitably configured to serve applications and data to a connected client 110.

In accordance with various embodiments, health records management system 115 is usable to: register and/or pre-register consumers for access to the system; provide consumers and healthcare providers access to health care records; generate health service reminders and/or notifications, for example immunization reminders; deliver data to, retrieve data from, and/or transfer data between one or more states, healthcare providers, and/or consumers; and/or the like. Continuing to reference FIG. 1, health records management system 115 utilizes and/or allows communication with a primary database 150, and with various other databases, tools, UIs and systems, for example external systems and databases 160. Such systems include, for example, state immunization registries, healthcare provider systems, third-party health records management systems (for example, the "Health Vault" product offered by Microsoft Corporation), and/or the like.

Health records management system 115 components may be interconnected and communicate with one another to allow for a completely integrated health records management system.

In various embodiments, certain health records management system 115 module(s) 145 are software modules configured to enable online functions such as sending and receiving messages, receiving query requests, configuring responses, dynamically configuring user interfaces, requesting data, receiving data, displaying data, executing complex processes, calculations, forecasts, mathematical techniques, workflows and/or algorithms, prompting user 105, verifying user responses, authenticating the user, initiating health records management system 115 processes, initiating other software modules, triggering downstream systems and processes, encrypting and decrypting, and/or the like. Additionally, health records management system 115 modules may include any hardware and/or software suitably configured to receive requests from client 110, for example via Internet server 125 and application server 142. It will be appreciated that, while module 145 is illustrated as a single module in FIG. 1, in various embodiments components of health records management system 115 (and/or functionality thereof) may be combined into fewer modules or components, or alternatively, divided into additional modules and/or components.

Health records management system 115 modules may be further configured to process requests, execute transactions, construct database queries, and/or execute queries against databases within system 115 (e.g., database 150), external data sources and/or temporary databases. In various embodiments, one or more health records management system 115 modules may be configured to execute application programming interfaces in order to communicate with a variety of messaging platforms, such as email systems, wireless communications systems, mobile communications systems, multimedia messaging service ("MMS") systems, short messaging service ("SMS") systems, and the like.

Health records management system 115 modules 145 may be configured to exchange data with other systems and application modules, for example, a state immunization registry, and/or the like. In various embodiments, health records management system 115 modules 145 may be configured to interact with sub-modules, other systems, or components thereof to perform complex calculations, retrieve additional data, format data into reports, create XML representations of data, construct markup language documents, construct, define or control UIs, and/or the like. Moreover, health records management system 115 modules may reside as standalone systems or tools, or may be incorporated with the application server 142 or any other health records management system 115 component as program code. As one of ordinary skill in the art will appreciate, health records management system 115 modules may be logically or physically divided into various subcomponents, such as a workflow engine configured to evaluate predefined rules and to automate processes.

In addition to the components described above, health records management system 115 may further include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; a plurality of databases; a network interface for communicating with external electronic devices; and/or the like.

As will be appreciated by one of ordinary skill in the art, one or more health records management system 115 components may be embodied as a customization of an existing system, an add-on product, upgraded software, a stand-alone system (e.g., kiosk), a distributed system, a method, a data processing system, a device for data processing, and/or a computer program product. Accordingly, individual health records management system 115 components may take the form of an entirely software embodiment, an entirely hardware embodiment, or an embodiment combining aspects of both software and hardware. Furthermore, individual health records management system 115 components may take the form of a computer program product on a computer-readable storage medium having computer-readable program code means embodied in the storage medium. Any suitable computer-readable storage medium may be utilized, including magnetic storage devices (e.g., hard disks), optical storage devices, (e.g., DVD-ROM, CD-ROM, etc.), electronic storage devices (e.g., flash memory), and/or the like.

As used herein, "computer-readable storage medium" does not include transitory phenomena such as propagating electromagnetic signals. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Client 110 may include an operating system as well as various conventional support software and drivers typically associated with mobile devices and/or computers. Client 110 may be in any environment with access to any network, including both wireless and wired network connections. In various embodiments, access is through a network or the Internet through a commercially available web-browser software package. Client 110 and health records management system 115 components may be independently, separately or collectively suitably coupled to the network via data links which include, for example, a connection to an Internet Service Provider (ISP) over the local loop as is typically used in connection with standard wireless communications networks and/or methods, such as modem communication, cable modem, satellite networks, ISDN, digital subscriber line (DSL), and/or the like. In various embodiments, any portion of client 110 may be partially or fully connected to a network using a wired ("hard wire") connection. As those skilled in the art will appreciate, client 110 and/or any of the system components may include wired and/or wireless portions.

In various embodiments, components, modules, and/or engines of health records management system 115 may be implemented as micro-applications or micro-apps. Micro-apps are typically deployed in the context of a mobile operating system, including for example, an Apple iOS, an Android operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

Internet server 125 may be configured to transmit data to client 110, for example within markup language documents. "Data" may include encompassing information such as commands, messages, transaction requests, queries, files, data for storage, and/or the like in digital or any other form. Internet server 125 may operate as a single entity in a single geographic location or as separate computing components located together or in separate geographic locations. Further, Internet server 125 may provide a suitable web site or other Internet-based graphical user interface, which is accessible by users (such as user 105). In various embodiments, Microsoft Internet Information Server, Microsoft Transaction Server (MTS), and Microsoft SQL Server, are used in conjunction with a Microsoft operating system, Microsoft NT web server software, a Microsoft SQL Server database system, and a Microsoft Commerce Server. In various embodiments, the well-known "LAMP" stack (Linux, Apache, MySQL, and PHP/Perl/Python) are used to enable health records management system 115. Additionally, components such as Access or Microsoft SQL Server, Oracle, Sybase, InterBase, etc., may be used to provide an Active Data Object (ADO) compliant database management system. In various exemplary embodiments, components of health records management system 115 may comprise and/ or utilize a HIPPA-compliant cloud computing resource, for example the Elastic Compute Cloud service offered by Amazon.com, and/or offerings from Rackspace.com, VMware, Windows Azure, and/or the like.

Like Internet server 125, application server 142 may communicate with any number of other servers, databases and/or components through any means known in the art. Further, application server 142 may serve as a conduit between client 110 and the various systems and components of health records management system 115. Internet server 125 may interface with application server 142 through any means known in the art including a LAN/WAN, for example. Application server 142 may further invoke software modules, such as system module(s) 145, automatically or in response to user 105 requests.

Any of the communications, inputs, storage, databases or displays discussed herein may be facilitated through a web site having web pages. The term "web page" as it is used herein is not meant to limit the type of documents and applications that may be used to interact with the user. For example, a typical web site may include, in addition to standard HTML documents, various forms, Java applets, JavaScript, active server pages (ASP), common gateway interface scripts (CGI), Flash files or modules, FLEX, ActionScript, extensible markup language (XML), dynamic HTML, cascading style sheets (CSS), helper applications, plug-ins, and/or the like.

With continuing reference to FIG. 1, databases are included in various embodiments. An exemplary list of various databases used herein includes: an authentication database 135, a user database 140, primary database 150 and/or other databases that aid in the functioning of the system. As practitioners will appreciate, while depicted as separate and/or independent entities for the purposes of illustration, databases residing within health records management system 115 may represent multiple hardware, software, database, data structure and networking components. Furthermore, embodiments are not limited to the databases described herein, nor do embodiments necessarily utilize each of the disclosed databases.

Authentication database 135 may store information used in an authentication process, for example user identifiers, passwords, access privileges, user preferences, user statistics, and the like. User database 140 maintains user information and credentials for health records management system 115 users (e.g., user 105).

In various embodiments, primary database 150 is a data repository that may be configured to store a wide variety of comprehensive data for health records management system 115. While depicted as a single logical entity in FIG. 1, those of skill in the art will appreciate that primary database 150 may, in various embodiments, consist of multiple physical and/or logical data sources. In various embodiments, primary database 150 stores one or more of consumer name, date of birth, street address, phone number, email address, password, security question and answer, gender, birth order, social security number, consumer relationship information (e.g., spouse, parent, child, guardian, dependent, etc.), immunization type and vaccine family information, immunization date information, administering provider, risk factors, age appropriate schedule of immunizations due or past due or next due, vaccine status (public vs. private), narrative content of an informational nature, and/or the like.

Any databases discussed herein may include relational, hierarchical, graphical, or object-oriented structure and/or any other database configurations. Common database products that may be used to implement the databases include DB2 by IBM (Armonk, NY), various database products available from Oracle Corporation (Redwood Shores, CA), Microsoft Access or Microsoft SQL Server by Microsoft Corporation (Redmond, Washington), MySQL by MySQL AB (Uppsala, Sweden), Ehcache, Couchbase, VoltDB, Versant, Hazelcast, or any other suitable database product, for example a persistent and distributed in-memory database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. Examples include distributing data elements to grid memory, optimizing partitioning of memory objects to process, indexing frequently used files and placing on separate file systems to reduce Input/Output ("I/O") bottlenecks.

One skilled in the art will also appreciate that, for security reasons, any databases, systems, devices, servers or other components of health records management system 115 may consist of any combination thereof at a single location or at multiple locations, wherein each database or system includes any of various suitable security features, such as firewalls, access codes, encryption, decryption, compression, decompression, and/or the like.

With continued reference to FIG. 1, in various embodiments, user 105 logs onto an application (e.g., a module) and Internet server 125 may invoke an application server 142. Application server 142 invokes logic in health records management system 115 modules by passing parameters relating to user's 105 requests for data. Health records management system 115 manages requests for data from health records management system 115 modules and/or communicates with internal and/or external components. Transmissions between user 105 and Internet server 125 may pass through a firewall 120 to help ensure the integrity of health records management system 115 components. Practitioners will appreciate that exemplary embodiments may incorporate any number of security schemes or none at all. In various embodiments, Internet server 125 receives requests from client 110 and interacts with various other health records management system 115 components to perform tasks related to requests from client 110.

Internet server 125 may invoke an authentication server 130 to verify the identity of user 105 and assign roles, access rights and/or permissions to user 105. For example, a user 105 may be a consumer, a health records provider, a state administrator, and so forth, and the rights, roles, permissions, and access thereof may be customized and/or limited, as desired. In order to control access to the application server 142 or other components of health records management system 115, Internet server 125 may invoke an authentication server 130 in response to user 105 submissions of authentication credentials received at Internet server 125. In response to a request to access health records management system 115 being received from Internet server 125, Internet server 125 determines if authentication is required and transmits a prompt to client 110. User 105 enters authentication data at client 110, which transmits the authentication data to Internet server 125. Internet server 125 passes the authentication data to authentication server 130 which queries the user database 140 for corresponding credentials. In response to user 105 being authenticated, user 105 may access various applications and their corresponding data sources.

Figure 2A:
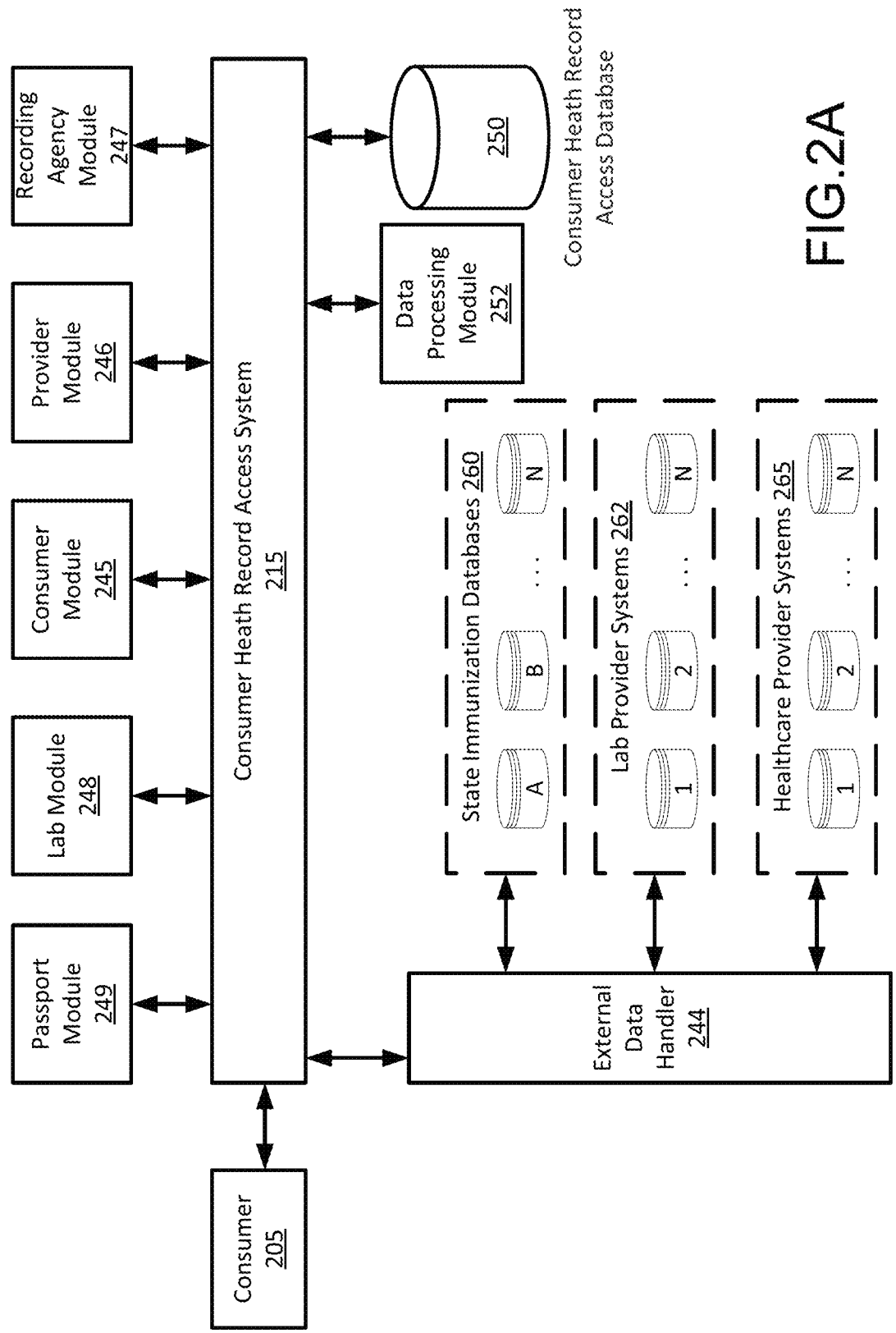
FIG. 2A is a block diagram illustrating exemplary consumer health record access system components, in accordance with various embodiments.
Figure 2B:
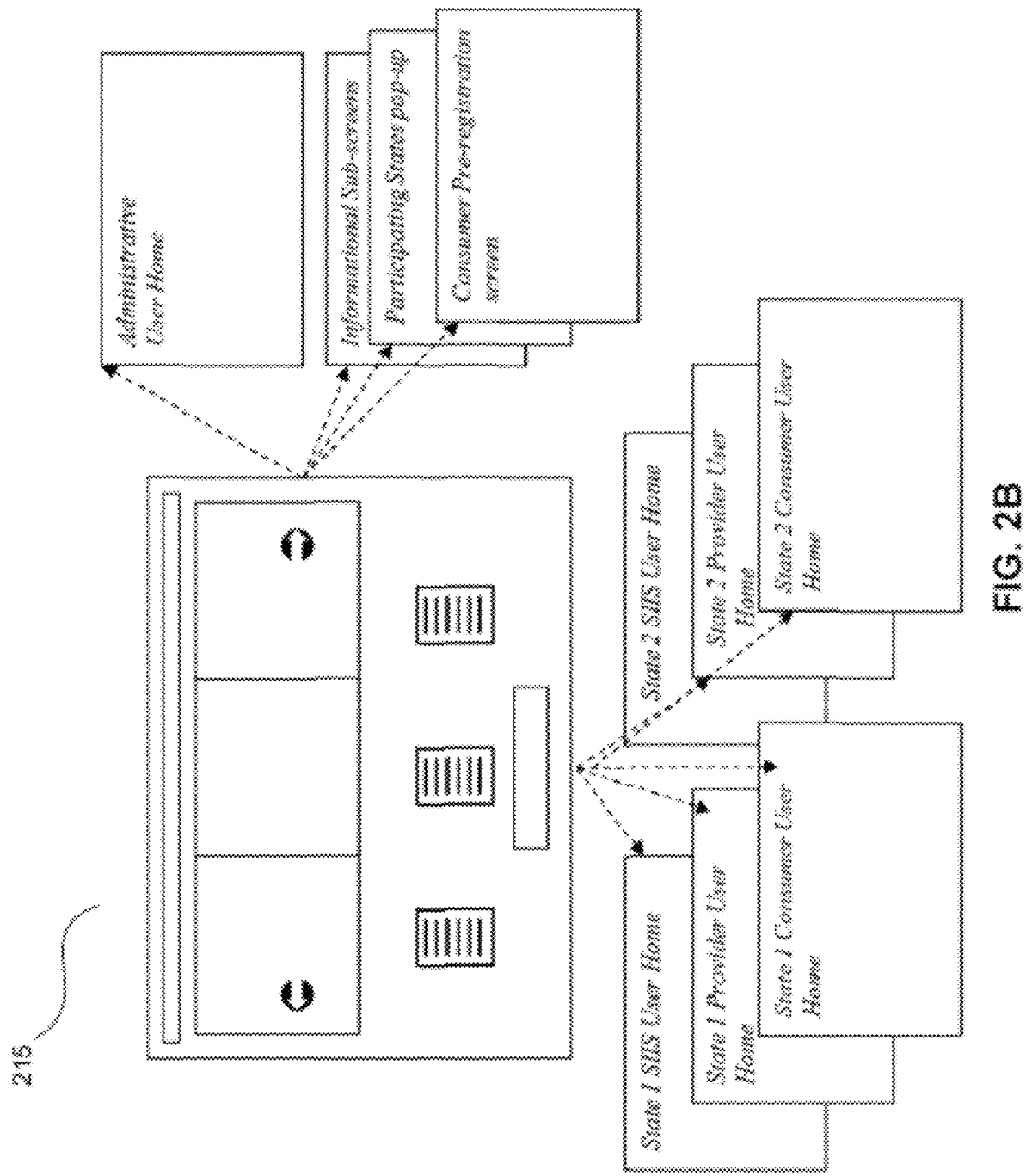
FIG. 2B illustrates exemplary screen layouts of an exemplary consumer health record access system in accordance with various embodiments.

With reference now to FIGS. 2A and 2B, in various embodiments, a health records management system 115 may be configured as software bus (consumer health record access system 215) which provides comprehensive access to immunization records, for example by and among recording agencies (i.e., state, national, and/or international government sanctioned databases), healthcare providers, and consumers. As opposed to prior systems wherein consumers were required to obtain immunization records from healthcare providers and/or directly from the recording agency, consumer health record access system 215 allows consumers to access immunization records from and/or deliver immunization records to one or more state immunization registries. Additionally, many states previously required that a consumer create a read-only account with a state immunization registry before viewing immunization records; in contrast, via use of consumer health record access system 215, consumers can both retrieve immunization records from a state as well as provide immunization records to a state (for example, a consumer can provide immunization records from State A to State B after the consumer moves from State A to State B).

System 115 may be computer based, and may comprise a processor, a tangible non-transitory computer-readable memory, and/or a network interface, along with other suitable system software and hardware components. Instructions stored on the tangible non-transitory memory may allow system 115 to perform various functions, as described herein. In various embodiments, the application server 115 and/or consumer heath record access system service (i.e., service 215) may be configured as a central network element or hub to access various systems, engines, and components of system 115.

In various exemplary embodiments, consumer health record access system 215 comprises consumer module 245, provider module 246, state module 247, lab module 248, passport module 248, external data handler 244, consumer health record access database 250, and data processing module 252. Consumer health record access system 215 may interface with and/or be capable of communication with one or more external data sources or databases such as, for example, state immunization databases 260 (e.g. State A, State B, State C, . . . State N), lab provider systems 262 (e.g., System 1, System 2, System 3, . . . System N), healthcare provider systems 265 (e.g. System 1, System 2, System 3 . . . System N), consumers/users 205, and/or the like. Consumer health record access system 215 may comprise various interactive web pages, software modules, and/or the like, for example as illustrated in FIG. 2B.

Consumer module 245 is configured for use by consumers. In various exemplary embodiments, consumer module 245 is configured to support registering consumers for an account, pending authentication/approval by a participating healthcare provider. Consumer module 245 provides a consumer with timely and relevant public and personal health information including but not limited to immunization-related information. Consumer module 245 also provides consumers with a mechanism to "cohort" (group together) family members under a single consumer account for the purposes of conveniently obtaining copies of their immunization records, for example once each family member is authenticated/approved by a participating healthcare provider.

In certain exemplary embodiments, consumer module 245 provides a consumer with an overview of all recorded immunizations for each approved family member. The source for the recorded immunization data may be any suitable source, but in various embodiments, the data source is the participating state(s) immunization information system or "registry".

Consumer module 245 is configured to provide a consumer with an immunization forecast (a schedule of recommended immunizations that are coming due, now due, or past due). The forecast may be generated based on any suitable factors. In certain embodiments, the forecast is determined in accordance with national recommendations from the U.S. Centers for Disease Control and Prevention, and/or from state-specific immunization schedule requirements.

Consumer module 245 is configured to provide a consumer with one or more electronic copies (for example, in PDF format) of an immunization record (for example, an immunization registry-based record) for each authenticated/approved family member. The records are formatted to conform in content and appearance, according to state-specific requirements.

Consumer module 245 provides a consumer with a feedback mechanism (for example, via a web forum), allowing the collection of user-experience, testimonials, and suggestions, and comprising a vehicle for the establishment of a community-of-users. Additionally, consumer module 245 provides a consumer with an automated reminder function that alerts the consumer (via various modalities) to immunizations that are coming due, now due, or past due for any authenticated/approved family member.

Yet further, consumer module 245 provides a consumer with a mechanism to share, at the consumer's discretion, copies of any of his or her immunization records with third parties (e.g., healthcare providers, a personal health record system, and/or the like) that can receive data formatted according to the federal BlueButton+ standards (a body of standards promulgated and maintained by the U.S. Department of Health and Human Services).

Consumer module 245 provides a consumer with the ability to report to various authorities any perceived discrepancy between their record content (for example, immunization record content) and their personal knowledge (or other source documentation) of their complete immunization history; this allows other authorized entities (e.g., participating healthcare provider) to investigate and resolve discrepancies. Consumer module 245 also provides consumers with non-immunization-related content and functionality, for example personal/household risk assessments, electronic connections with other public health program agencies, preventive health services information, and opportunities to volunteer for participation in state-specific public health oriented surveys, studies, and trials. Consumer module 245 may also provide program, provider, or services locator functionality, or interface with downloadable application(s) for use with smartphone devices and tablet computers.

Consumer module 245 provides a consumer with age-appropriate anticipatory guidance materials for childhood-related health risks, with a look-up feature for participating healthcare providers, and with the ability to obtain electronic copies of immunization records from any state that participates with consumer health record access system 215 (and for which the consumer and their family member(s) have been authenticated and approved in the respective states).

With continued reference to FIG. 2A, provider module 246 is configured for use by healthcare providers. In various exemplary embodiments, provider module 246 allows providers to register and authenticate/approve consumers who request an account, including family members for which he or she requests records access.

Provider module 246 allows providers to look-up consumers who have registered (pending authentication/approval) and to authenticate and approve or reject consumer requests for an account. Moreover, provider module 246 provides providers with relevant public health and personal health information applicable to immunizations as well as other topics.

In certain exemplary embodiments, provider module 246 provides providers with peer-reviewed tools, guidance documents, and patient educational materials pertinent to immunizations, captures demographic and practice-specific information specific to participating providers, and allows provider look-up of view-only records within the state-specific Immunization Information System to which they have been granted approved access.

Provider module 246 may be configured to allow providers to deactivate (suspend) records access permission for any approved consumer or family member. Provider module 246 provides providers with metrics regarding the nature and frequency of consumer health record access system 215 usage by consumers for which the provider has authenticated/approved access.

In various exemplary embodiments, provider module 246 provides providers a user feedback mechanism (for example a web forum, chat room, and/or the like) to allow sharing of comments, suggestions, testimonials, etc., and to create a community of users. Additionally, provider module 246 provides providers a mechanism by which consumers can submit reports of record discrepancies, for example via transmissions using the federal BlueButton+ data exchange standards. Moreover, provider module 246 allows providers to receive the results of consumer risk assessments and other consumer-initiated health information from consumers that voluntarily seek to provide such information to their healthcare provider.

Provider module 246 can provide providers a mechanism to view alerts and other information posted by authorities at the respective state immunization program or registry. Provider module 246 may be configured with a remote lookup capability wherein a provider may view, in read only mode, immunization records for any resident of a state, even if such resident is not a patient of the provider.

With continued reference to FIG. 2, recording agency module 247 is configured for use by recording agency representatives (e.g., state representatives). For example, recording agency module 247 allows recording agency administrative representatives to create new provider accounts, allows state administrative representatives to deactivate (suspend) previously created provider accounts, and allows recording agency administrative representatives to deactivate (suspend) the accounts of any previously authenticate/approved consumer or family member.

In various exemplary embodiments, recording agency module 247 allows recording agency administrative representatives to create and post informational content (e.g., alerts, guidance, public health information, etc.) to a recording agency specific consumer web page or provider web page. Additionally, recording agency module 247 allows recording agency administrative representatives to view various metrics summarizing system performance and/or pertaining to system usage by consumer and provider account-holders.

In some exemplary embodiments, recording agency module 247 allows recording agency administrative representatives to communicate via e-mail with consumer and provider account-holders, to manage various configurable settings governing recording agency specific application behavior and functionality, and to receive transmissions from account holders sent via BlueButton+ standards. Recording agency module 247 may be configured with analytics capabilities to allow recording agency representatives to visualize trending, provider referral details, and otherwise analyze system use by consumers in their jurisdiction. Recording agency module 247 may also comprise and/or be configured with forecasting tools, for example in order to evaluate potential future immunization needs or other modeled public health requirements or outcomes.

With continued reference to FIG. 2A, lab module 248 is configured for use by lab providers. In various exemplary embodiments, lab module 248 allows lab providers to register and authenticate/approve consumers who request an account, including healthcare providers and/or family members for which he or she requests records access.

Lab module 248 allows providers to look-up consumers who have registered (pending authentication/approval) and to authenticate and approve or reject consumer requests for an account. Moreover, lab module 248 provides providers with relevant public health and personal health information applicable to lab work and immunizations as well as other topics.

In certain exemplary embodiments, lab module 248 provides lab providers with peer-reviewed tools, guidance documents, and patient educational materials pertinent to lab work, captures demographic and practice-specific information specific to participating providers, and allows provider look-up of view-only records within the state-specific healthcare database systems (e.g., healthcare information exchanges, IIS, etc.) which they have been granted approved access.

Lab module 248 may be configured to allow providers to deactivate (suspend) records access permission for any approved consumer, healthcare provider, or family member. Lab module 248 provides providers with metrics regarding the nature and frequency of consumer health record access system 215 usage by consumers for which the provider has authenticated/approved access.

In various exemplary embodiments, lab module 248 provides providers a user feedback mechanism (for example a web forum, chat room, and/or the like) to allow sharing of comments, suggestions, testimonials, etc., and to create a community of users. Additionally, provider module 246 provides providers a mechanism by which consumers can submit reports of record discrepancies, for example via transmissions using the federal BlueButton+ data exchange standards. Moreover, lab module 248 may enable providers to receive the results of consumer risk assessments and other consumer-initiated health information from consumers that voluntarily seek to provide such information to their healthcare provider.

Lab module 248 can provide providers a mechanism to view alerts and other information posted by authorities at the respective state immunization program or registry. Lab module 248 may be configured with a remote lookup capability wherein a provider may view, in read only mode, immunization records for any resident of a state, even if such resident is not a patient of the provider.

In various embodiments and with continued reference to FIG. 2A, passport module 249 is configured to compile consumer health records to generate passport report data and to deliver the passport report data to passport data users. The passport module may compile data from state immunization databases 260, lab provider systems 262, and healthcare provider systems 265 to generate the passport report data. The system may store the passport report data in consumer health record access database 250. In various embodiments, the passport report data may comprise a record of immunizations associated with a consumer health record, immunization-related information, lab related information (e.g., test results, test dates, etc.), and/or the like.

Passport module 249 may comprise an application program interface configured to provide a programmatic interface to any of the set of system 215 services, components, modules, and/or engines. In various embodiments, the passport module 249 may be configured to generate a matrix barcode such as, for example, a QR code comprising the passport report data. The passport module 249 may be configured to enable the matrix barcode comprising the passport report data to be displayed on a user device. In this regard, the passport module 249 may enable transfer of passport report data to third parties which may read the displayed matrix barcode. For example an entertainment venue may request the passport report data associated with a consumer who whishes to enter the venue. System 215 may receive the passport report data request and, in response, compile the database data to generate the passport report data. The system may pass the passport report data to the venue via the API or the matrix barcode.

Consumer health record access database 250 stores information utilized by consumer health record access system 215, for example information similar to information stored in primary database 150. The database 250 may comprise a plurality of consumer accounts and a plurality of health records. Each consumer account may have one or more of the plurality of health records stored in association therewith. In this regard, the consumer health record access database may comprise a plurality health records associated on a many to one basis with each of a plurality of consumer accounts. For example, a consumer account may be associated with eleven health records. In various embodiments, a first patient name may be associated with four of the health records associated with the consumer account and a second patient name may be associated with the remaining seven of the health records associated with the consumer account.

In various exemplary embodiments, consumer health record access system 215 is configured to provide bi-directional Health Level 7 (HL7) messaging capability to state immunization registries and health care providers. For example, the system may communicate using HL7 Update (VXU) and Query (QBP) messages.

In various embodiments, data processing module 252 is configured to apply algorithmic transformations and analysis to health records of the database 250. Data processing module 252 may be configured to perform deduplication operations, record merging operations, record linking operations, and or the like. In various embodiments, the data processing module 252 may be configured to execute machine learning algorithms such as, for example, supervised or semi-supervised machine learning algorithms.

In various embodiments, data processing module 252 may be configured to identify health records where name elements are similar. The data processing module 252 may sort the health records for records where the first name element is null, the last name element is null, and/or the birth date element is null. Records where any of these elements are null may be excluded from further processing by the data processing module 252. The data processing module may further process the remining health records apply a hashing function to each of the remaining health records.

In various embodiments, misspellings of name elements (e.g., the first name element, the last name element) may be frequent errors in the health record data. The hash function may be a function of the first name initial, the last name initial, and a combined first name character length and last name character length. In this regard, the system may process duplicate records which have been entered based on errors introduced in name elements. For example, hashing the text string 'Sawyer Koops' may return an identical output to hashing the text string 'Samuel Krebs.' In contrast, hashing the text string 'Sawer Koops' may return a different output to hashing the text string 'Sawyer Koops.' In various embodiments, the hash function may be based on record elements comprising one of a first name, a last name, a date of birth, a first name character length, a last name character length, a combined first and last name character length, a date of birth year, a first name initial, or a last name initial. In this regard, the data processing module 252 may be configured to perform deterministic error detection of duplicate records.

In various embodiments, the data processing module 252 may selectively apply a first hashing function, a second hashing function, a third hashing function, and/or a fourth hashing function. Each hashing function may return an eight digit integer output and the system may generate a hash index based on the hash function output. Each hash of the hash index may be associated on a one-to-one basis with each record of the plurality of health records selected for further processing. The system may generate a hash index for each of the hash functions and may generate a hash table comprising each of the hash indexes. In various embodiments, the system may identify matching hashes within the hash index and/or across the hash table. In this regard, by analysis of the hash output, the data processing module 252 may be configured to perform error detection for duplicate records in a deterministic process. The system may flag records associated with the matching hashes of the hash index and or matches across the hash table for further processing by non-determinist machine learning algorithms and/or review by a user. For example, the system may apply the first hashing function to generate a first hash index, apply the second hashing function to generate a second hash index, and apply the third hash function to generate a third hash index. The system may merge each of the first hash index, the second hash index, and the third hash index to generate a hash table. The system may identify matches across the hash table and flag the records associated with the cross-table matches for further processing (i.e., those where the outputs of each of different hashing functions match).

In various embodiments, the first hashing function may be based on the first name initial, the first name character length, the last name initial, and the last name character length. In this regard, the first hashing function treats the treats first name and last name lengths separately. The first hashing function may not allow for nearest neighbor identification where errors such as an extra or missed keystroke in either the first name element or last name element are present. For example, an extra or missed character in the first name element will move similar people dramatically further away (as calculated based on the hash output value) as a potential match when the hash value is indexed across the hash table. Practically, the first hashing function would tend to inhibit 'SAWER KOOPS' (first name character length of 5 and returning, for example 29052105) from ending up matching or near the hash for 'SAWYER KOOPS' (first name character length of 6 and returning, for example, 29062105).

In various embodiments, the second hashing function may be based on the first two characters of the first name element, the first two characters of the last name element, and the combined first and last name character length. In various embodiments, the third hashing function may be based on the first name initial, the date of birth year, and the combined first and last name character length. In various embodiments, the fourth hashing function may be based on the first name initial, the last name initial, and the combined first and last name character length. In various embodiments, the first and second digits of the eight digit integer output of a hashing function may encode the first name initial, the third and fourth digits of the eight digit integer may encode the last name initial, and the remining digits may encode the combined first and last name character length. In various embodiments, the fifth and sixth digits of the eight digit integer output of the hashing function may be forced to a null value.

In various embodiments, the hash function may return a measure of similarity between first name elements and last name elements used as inputs to the hash function. In this regard data processing module 252 may identify merged records—i.e. where one record is associated with information from two different underlying individuals. For example, in a data environment where a key field (e.g., a patient ID), is associated with several first name elements and last name elements, a merged record may comprise two name elements with each of the name elements including a respective first name element and a last name element (i.e. 'Sawyer Koops' and 'Michael Jones'). The system may apply the hashing function to all name elements within a plurality of records. The system may remove from the record set all records where the hashing function returns identical values for the name elements to generate a merge error record set.

Figure 11A:
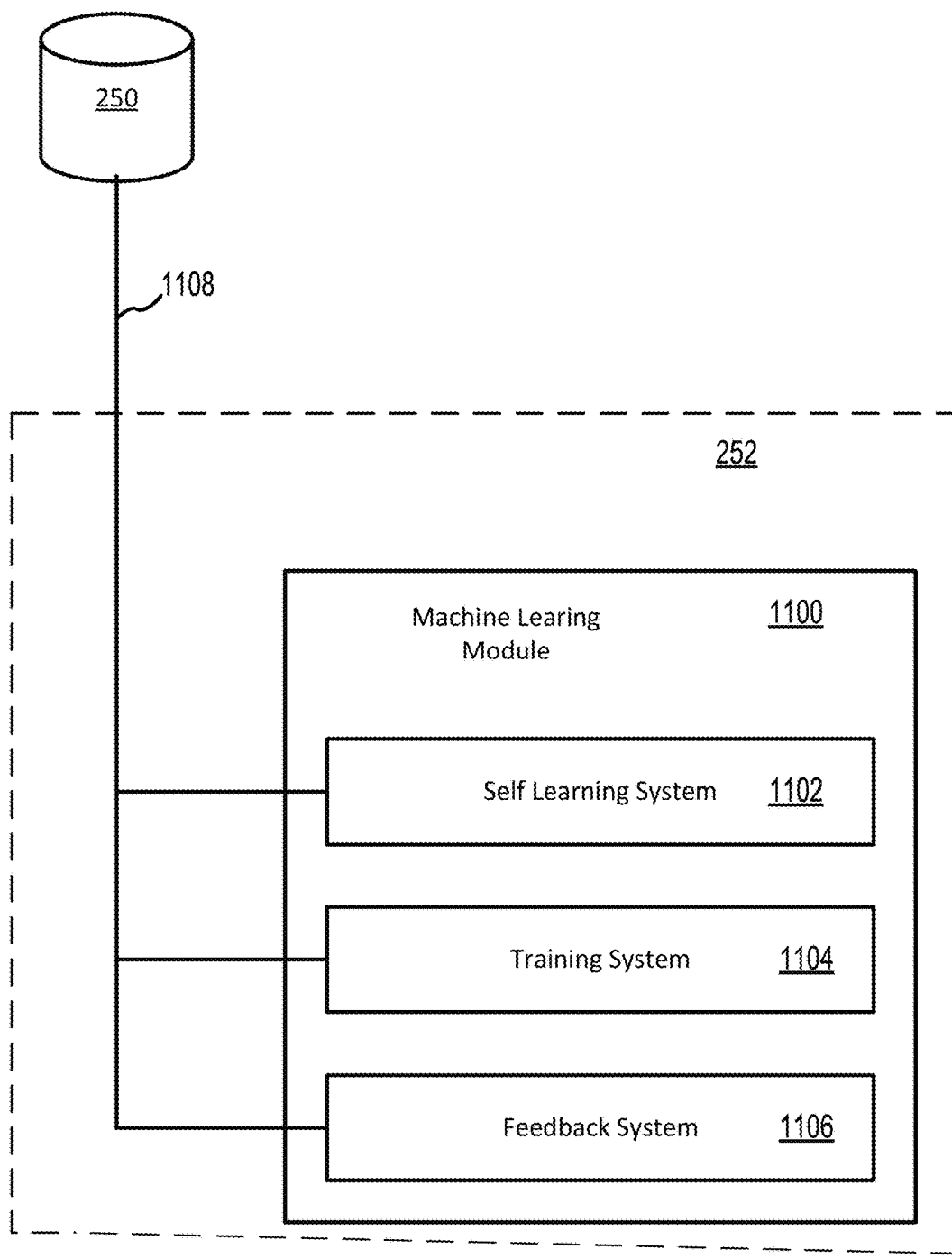
FIG. 11A illustrates a machine learning module in an exemplary consumer health record access system in accordance with various embodiments.
Figure 11B:
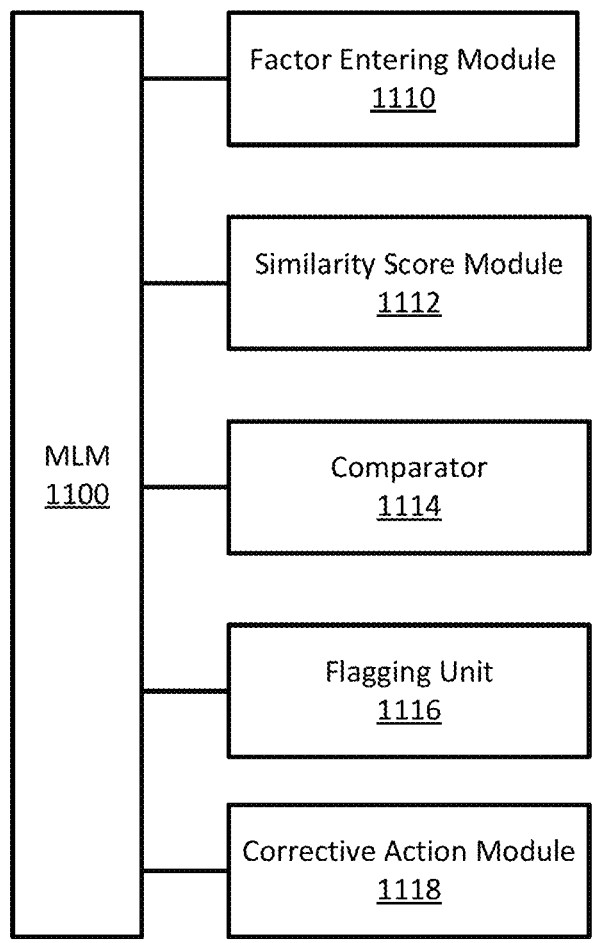
FIG. 11B illustrates a machine learning module an exemplary consumer health record access system in accordance with various embodiments.

With additional reference to FIGS. 11A and 11B, the system may apply a Machine Learning Module (MLM) 1100 to each of the records in the merge error record set. The MLM may comprise a machine learning based algorithm which may look across rows of each of the records and return clusters based on the rows. The system may calculate a similarity score for each record i.e. a measure of the relatedness of the records to one another. The system may flag clusters of rows which exceed a similarity threshold value for further processing and/or analysis by a user. The system may flag clusters of rows that exceed a dissimilarity threshold value for further processing and/or analysis by a user. For example, the system may apply the MLM to each health record of a set of incoming health records received via bi-directional HL7 messaging from a healthcare provider or a state immunization registry the system may calculate the similarity score for each of the incoming records and compare the similarity score to those of existing records in the consumer health record access database. Where records are similar, the incoming record may be merged with the existing record in the database. Where records are dissimilar, the system may store the incoming record as a new record in the database. In various embodiments, the hash function may be applied to the incoming set or records and the existing records in the database. The system may generate an incoming record comparison set comprising a reduced set of the existing records of the database containing only those records having a hash output matching the hash output based on the incoming record. In this regard, by applying the MLM to only the incoming records and the reduced record set, the system may tend to reduce data processing time, increase processor overhead, increase data accuracy, and reduce system energy usage.

The machine learning algorithm may be a semi-supervised algorithm in communication with the databases (e.g. database 250) via the data processing module 252. The purpose of the MLM 1100 is to flag select records as described above with a merging error and to provide an interface for users to take further action to correct the merging error. The MLM 1100 may include a feedback system 1102, a training system 1104, and a self learning system 1106 connected to the database. During initial training, the training system 1104 is executed. The training system 1104 functions to train the MLM 1100. The training system 1104 receives data over the data retrieval channel 1108 from the database. The feedback system 1106 and the self learning system 1102 are not executed during initial training. The purpose of the training is to generate a first similarity score model including an initial set of weights assigned to an initial set of factors of the plurality of factors used by the Similarity Score Module (1112) to calculate a similarity score.

During continued operation, the feedback system 1106, training system 1104, and self learning system 1106 are executed, typically in sequence after one another. All three systems of the MLM 1100 receive data over the data retrieval channel 1108 from the database. The feedback system 1106 provides input into the training system 1104, the training system 1104 then provides input into the self learning system 1102. The self leaning system 1102 provides input into the MLM 1100 for the purposes of making adjustments to the similarity score model where necessary. For example the training system may use a training data set of health records, which does not include all of the records within the databases, to adjust the set of weights associated with factors and/or addition or subtraction of factors used in calculating the similarity score. In this regard, the self learning system may generate a second similarity score model having a second set of weights associated with a second set of factors of the plurality of factors. For the same data, the scores will be different between the first model and the second model. The system may continually update the set of weights and associated factors included in the similarity score model and thereby improve the accuracy of the similarity score over time. Factors can be added or deleted from the model depending on their relevance to providing the similarity score. Factors that are relevant may be retained and/or added over time or may be weighted differently over time to improve function of the similarity score model and improve the relevance of the similarity score to the design purpose of measuring relatedness of each of the health records. Factors that are irrelevant may be excluded from the similarity score model but may be re-included based on operational feedback from the feedback system 1106 and/or training system 1104.

With reference to FIG. 11B, the DMM core 1100 includes a Factor Entering Module 1110 (FEM), Similarity Score Module 1112 (SSM), a comparator 1114, a flagging unit 1116, and a Corrective Action Module 1118 (CAM). The FEM 1110 is a multi-factor entering module which enters a plurality of factors taken from the record elements of the plurality of records and/or the merge error record set associated with the key field and/or patient ID. The factors received and entered by the FEM 1110 may include record elements such as: a first name, a last name, a birth date, a street address, gender, a taxpayer ID number or social security number, zip code, birth order, birth year, city, state, country, race, ethnicity, email address, birth date, insurance ID number, maiden name, guardian name, alias, census tract, and or the like. The FEM 1110 is executable to enter the factors into the SSM 1112.

The SSM 1112 is executable to determine a similarity score for each one of the records, with the respective similarity score being based on weights assigned to the plurality of factors entered by the FEM 1110. The DMM 1110 may store the similarity score as metadata associated with the record, record elements, and/or patient ID. The comparator 1114 may evaluate the similarity scores and determine based on the similarity score which records to pass to the flagging unit 1116. In various embodiments, the flagging unit may flag records with high similarity or low similarity or based on the similarity score exceeding the similarity threshold value or dissimilarity threshold value. In this regard, the flagging unit 1116 may flag records for de-mering (separation and storage as discreet records) or may flag records for collation (combination into a single record). The flagging unit may flag consumer accounts comprising records which exceed the similarity or dissimilarity threshold value. In this regard, the flagging unit 1116 may indicate consumer accounts with a merging error in need of review for corrective action. The flagging unit 1116 may pass the flagged records and/or the consumer account to the corrective action module 1118 for further processing based on the appropriate corrective action.

In various embodiments, the flagging unit 1116 may flag records for automatic merging where the similarity score for matched records (e.g., those flagged as cross-table matches described above) is above the similarity threshold. The similarity score may be a decimal value between 0 and 1. The similarity threshold may be a decimal value which may be configured by the investigator. For example, the similarity threshold may be set such that where the similarity score of matched records is at least 0.90 and above, or at least 0.92 and above, or at least 0.94 and above the flagging unit 1116 may flag the records for automatic merging. An another example, the flagging unit 1116 may flag records for automatic de-merging where the similarity score for matched records (e.g., those flagged as cross-table matches described above) falls below the dissimilarity threshold. For example, the dissimilarity threshold may be set such that where the similarity score of matched records is at most 0.10 and below, or at most 0.08 and below, or at most 0.06 and below the flagging unit 1116 may flag the records for automatic de-merging. In various embodiments, where the similarity score is below the similarity threshold (or below the similarity threshold but above the dissimilarity threshold) the flagging unit 1116 may flag the records for further processing by the corrective action module 1118 as requiring corrective action or investigator review. In various embodiments, the system may flag records flagged for automatic merging or automatic de-merging as requiring corrective action. It will be appreciated that the processes of matching, flagging, merging, de-merging may be synchronous or asynchronous.

The corrective action module 1118 may be configured to perform a corrective action only for those consumer accounts which have health records flagged by the flagging unit as requiring corrective action. For example, for records which are flagged as described in the above example as requiring corrective action or investigator review (e.g., below the similarity threshold), the corrective action module 1118 may enable an investigator to execute a de-merging operation on the records. The system may prompt the investigator for feedback as to whether the records are in fact dissimilar. For records which are flagged as exceeding the similarity threshold value, the corrective action module 1118 may enable an investigator to execute a merging operation on the records. The system may prompt the investigator for feedback as to whether the records are in fact similar.

In various embodiments, the system may receive training inputs via the feedback system 1106 based on the corrective actions executed in the corrective action module 1118. The feedback may be input into the self learning system 1102 and thereby update the similarity model. In this regard, the record evaluations of the flagged records from the corrective action module 1118 may be logged and stored by the system as a means of retrospective feedback. The feedback may be aggregated and presented back to the investigator via the corrective action module 1118 to inform tuning of the SSM 1112 similarity score model. In this regard, the SSM 1112 and the corrective action module 1118 may (via feedback system 1106) enable synchronous or asynchronous self-referential feedback and model retraining based on investigator-directed decisions. In various embodiments, the corrective action module 1118 may enable setting and/or adjustment of the similarity threshold value and the dissimilarity threshold value. In various embodiments, the feedback from the corrective action module 1118 may be systematically sent to an external system for remote monitoring.

In various exemplary embodiments, consumer health record access system 215 is configured to provide a state-specific or state-required immunization report or certification form, for example as illustrated in FIG. 2F. Such reports may take the form of official state forms. Stated another way, consumers can access immunization documentation in both informal (i.e., report) form, as well as in formal (i.e., official state documentation) form. In this manner, states can simplify access to and distribution of official state immunization information and forms to consumers.

In various exemplary embodiments, consumer health record access system 215 is configured to provide state immunization administrators with a set of pre-defined and/or customizable web pages with communication and/or messaging capabilities. In this manner, state subscribers to consumer health record access system 215 can communicate to consumers in their state, for example to provide news, alerts, and so forth.

Figure 2E:
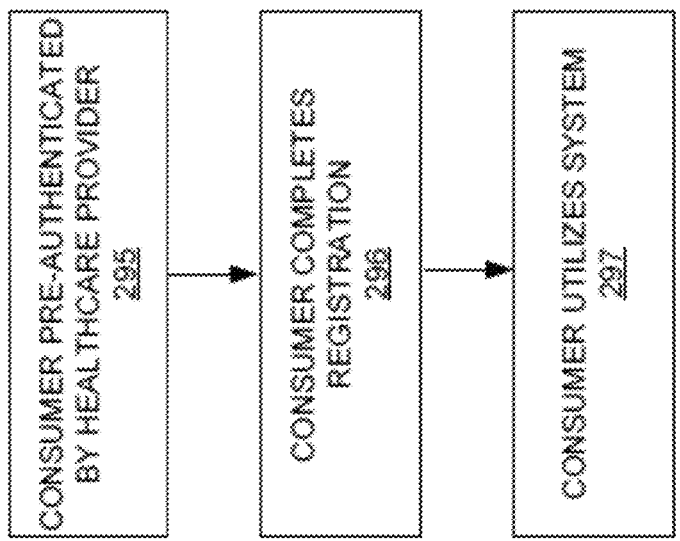
FIGS. 2C through 2E illustrate methods of registering a consumer in an exemplary consumer health record access system in accordance with various embodiments.
Figure 2D:
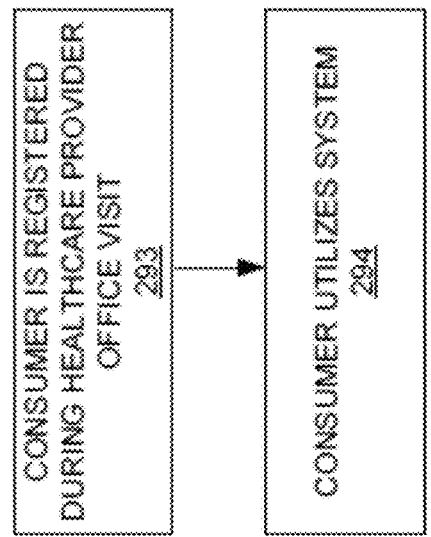
Figure 2C:
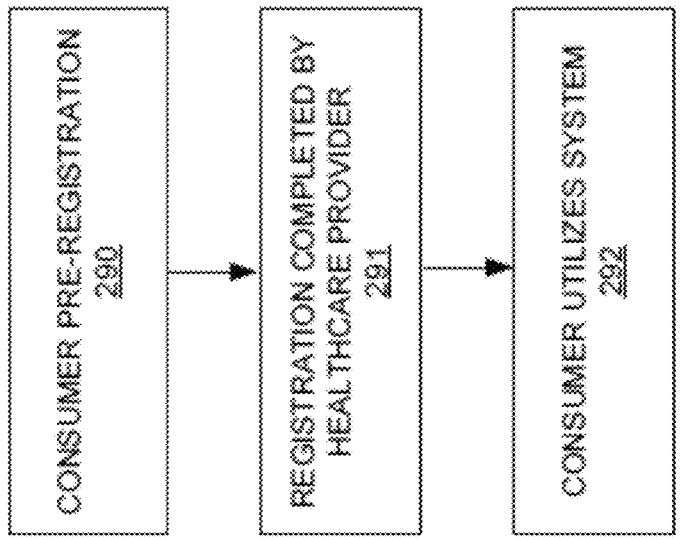
Figure 2F:
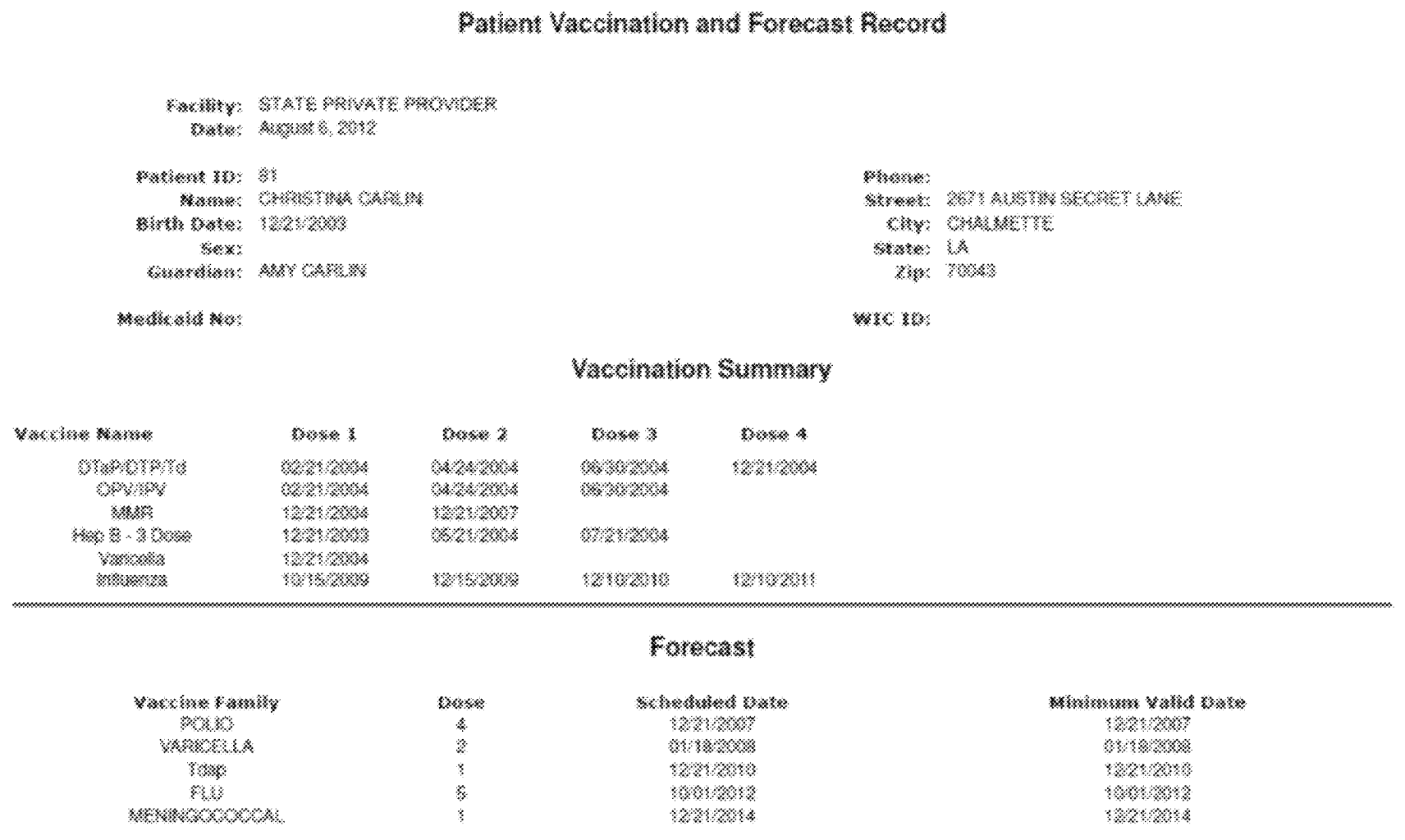

With reference now to FIG. 2C, in an exemplary embodiment a consumer pre-registers for access to consumer health record access system 215 (step 290). The consumer registration is completed during an office visit with a healthcare provider (step 291). The consumer may thereafter utilize the features of consumer health record access system 215 (step 292).

Turning now to FIG. 2D, in other exemplary embodiments, consumer registration is initiated and completed during an office visit with a healthcare provider (step 293). The consumer may thereafter utilize the features of consumer health record access system 215 (step 294).

Turning now to FIG. 2E, in other exemplary embodiments, a consumer is pre-authenticated by a healthcare provider (step 295). The consumer later completes the registration process (step 296). The consumer may thereafter utilize the features of consumer health record access system 215 (step 297).

"Registration" and/or "pre-registration" as utilized herein may be via any suitable method or system as known in the art, for example via username and password, welcome email and PIN, or other suitable authentication system.

In various exemplary embodiments, consumer health record access system 215 is configured to provide state-specific or state-required immunization reports or certification forms, for example as illustrated in FIG. 2F. Such reports may take the form of official state forms. Stated another way, consumers can access immunization documentation in both informal (i.e., report) form, as well as in formal (i.e., official state documentation) form. In this manner, states can simplify access to and distribution of official state immunization information and forms to consumers.

In various exemplary embodiments, when a consumer moves from State A to State B, the consumer will retain access in consumer health record access system 215 to records from State A, even after being authenticated into new State B. In this manner, centralized access to immunization records is facilitated. Via consumer health record access system 215, a consumer may also share records among states; i.e., a consumer may provide State B immunization information to State A to update the records of State A. Yet further, via consumer health record access system 215, a consumer may instruct that immunization records be provided, in a standardized format and/or protocol such as BlueButton+, to any external record acceptor (for example, healthcare providers, Microsoft Health Vault, and/or the like).

In various exemplary embodiments, consumer health record access system 215 checks immunization records in consumer health record access database 250 on a regular basis (for example, daily, weekly, bi-weekly, monthly, and so forth). Consumer health record access system 215 may be configured to send automated reminders to consumers and/or health care providers regarding upcoming scheduled immunizations, past due immunizations, supplementary recommended immunizations due to public health alerts, and/or the like.

In certain exemplary embodiments, consumer health record access system 215 provides "cohorting" capabilities to a consumer. In these embodiments, a particular consumer (e.g., a parent or guardian) may view and/or access immunization information for other consumers (e.g., a child or ward). In this manner, household immunization information may be centralized, facilitating improved immunization outcomes. For example, an adoptive parent may quickly determine that a particular child lacks a certain immunization previously received by other children in the same household; the parent can then schedule the suggested immunization.

In various exemplary embodiments, consumer health record access system 215 is usable to provide actionable information directly to a consumer based on at least one of the consumer's immunization history, age, gender, or risk. Consumer health record access system 215 supports interjurisdictional information retrieval, allowing a consumer to access his or her immunization records, either alone or in connection with the records of one of more family members, from multiple states. Consumer health record access system 215 is configured to provide seamless integration with other medical records systems, for example as found in retail health, clinical or personal health records, health information exchanges, and the like. Consumer health record access system 215 can provide consumer prevention information, screening data components, medical device integration, family pet immunization histories, and so forth.

In various exemplary embodiments, consumer health record access system 215 allows consumers to pre-register for an account, for example by specifying their desired password and e-mail address. Additionally, consumer health record access system 215 provides consumer-managed cohorting of family members. For example, consumer health record access system 215 can send requests for records access to a provider approval queue for any family member for which a consumer may request records access. Yet further, consumer health record access system 215 allows for provider-managed consumer registration/approval; this approach allows providers to optionally register and approve consumers in their healthcare setting.

In certain exemplary embodiments, consumer health record access system 215 is configured to support provider look-up of matching and/or closely matching records. For example, consumer health record access system 215 allows providers to view, within consumer health record access system 215, attributes of matching or closely matching records, for example records located through an HL7 query to a respective state immunization information system.

Consumer health record access system 215 is configured to provide immunization records reports and/or certificates. In one embodiment, consumer health record access system 215 allows consumers one generic and one or more state-specific views of immunization records that can be printed, stored, or pushed to other destinations.

Consumer health record access system 215 provides third-party consumer and provider educational information and tools. For example, consumer health record access system 215 provides ongoing access to archival and new peer-reviewed reference and educational materials targeted at consumers and providers (respectively).

In some exemplary embodiments, consumer health record access system 215 is configured with BlueButton+ capability. In this manner, consumer health record access system 215 may export copies of immunization records in the federal BlueButton+ format, enabling consumers to share their immunization records with providers and/or personal health records (PHR) service providers or software of their choosing.

Consumer health record access system 215 is configured to provide system performance metrics and analytics. This allows authorized administrative users to monitor system performance, attributes of users, system behavior and usage patterns. Additionally, consumer health record access system 215 is configured with a scalable user interface, permitting consumer health record access system 215 to be accessed and/or utilized on different devices (e.g., computer, tablet, smartphone).

Consumer health record access system 215 is interoperable with any HL7-compliant state immunization registry. In this manner, consumer health record access system 215 may be subscribed to by any state immunization registry.

Moreover, consumer health record access system 215 provides anticipatory guidance (preventive health) information for age-appropriate cohorts of children via consumer accounts, provides consumer health/household risk assessment instruments and analyses, and provides a communications exchange with various public health program areas of a topical nature.

In some exemplary embodiments, consumer health record access system 215 provides automated reminders for immunization and additional preventive health care-associated circumstances, provides provider and preventive services access and locational look-up features, and provides consumer alerting of healthcare providers to possible errors in record content.

Figure 3A:
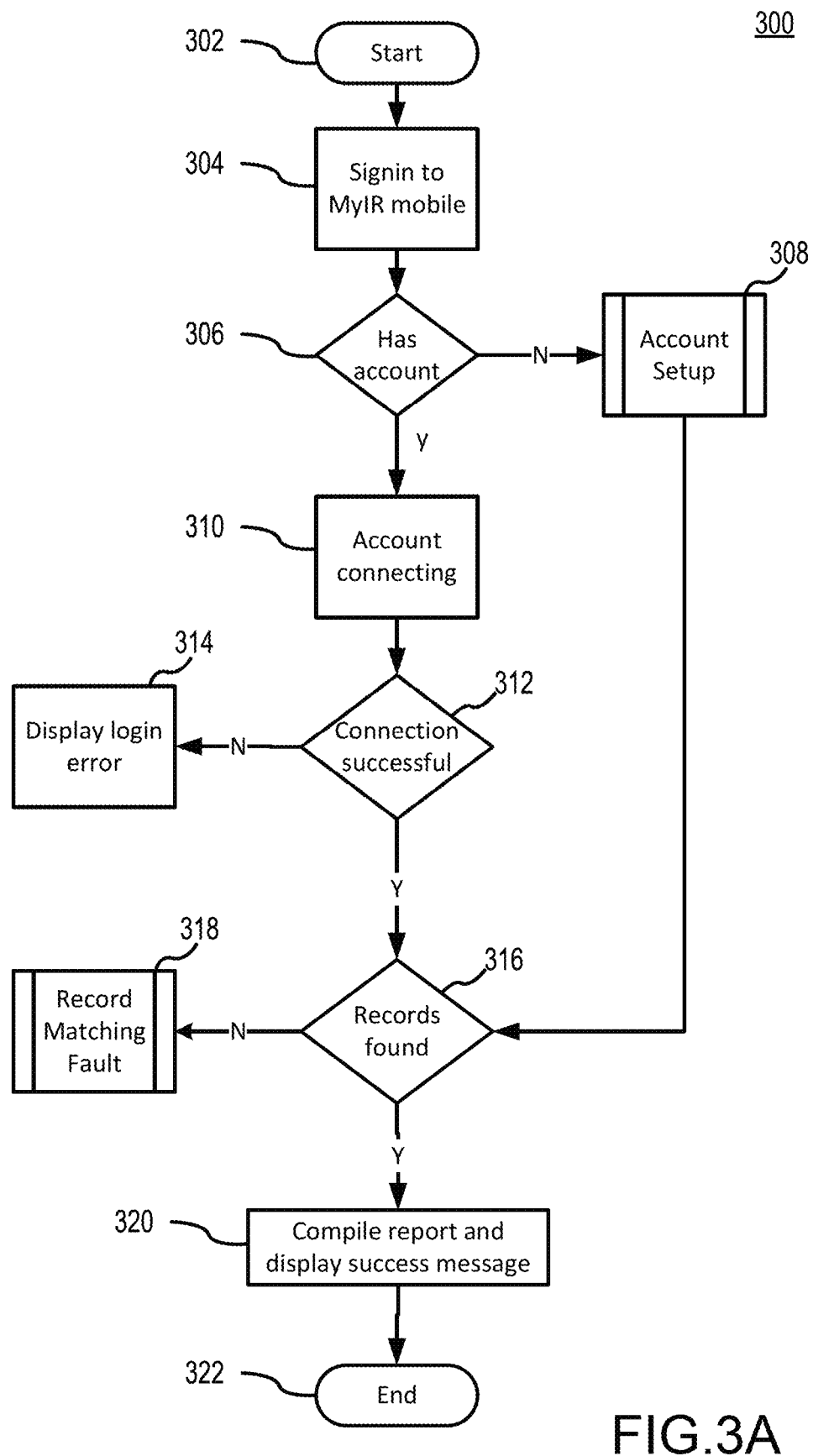
FIG. 3A illustrates a process for generating a passport report of an exemplary consumer health record access system in accordance with various embodiments.
Figure 3B:
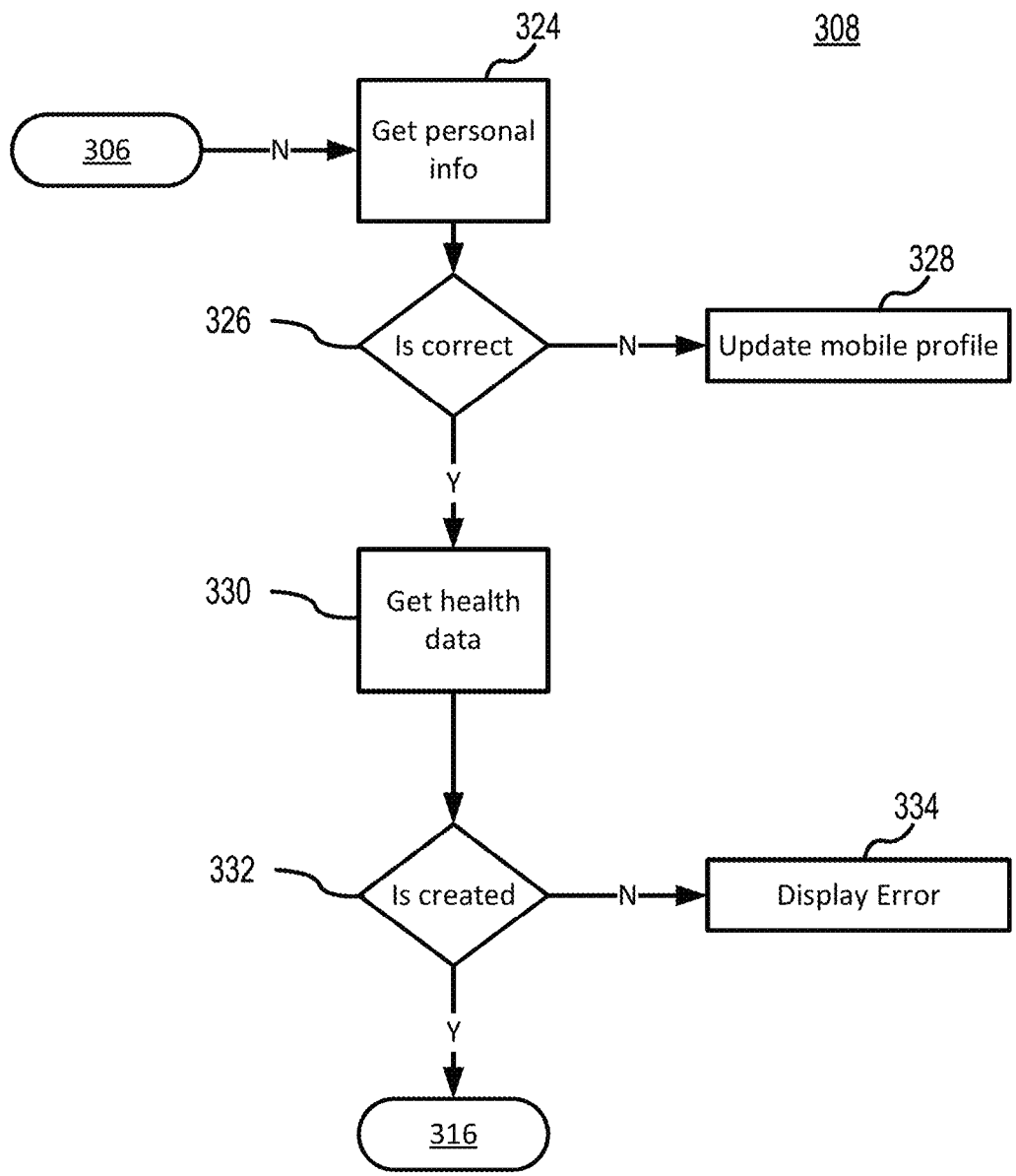
FIG. 3B illustrates an account setup process in an exemplary consumer health record access system in accordance with various embodiments.
Figure 3C:
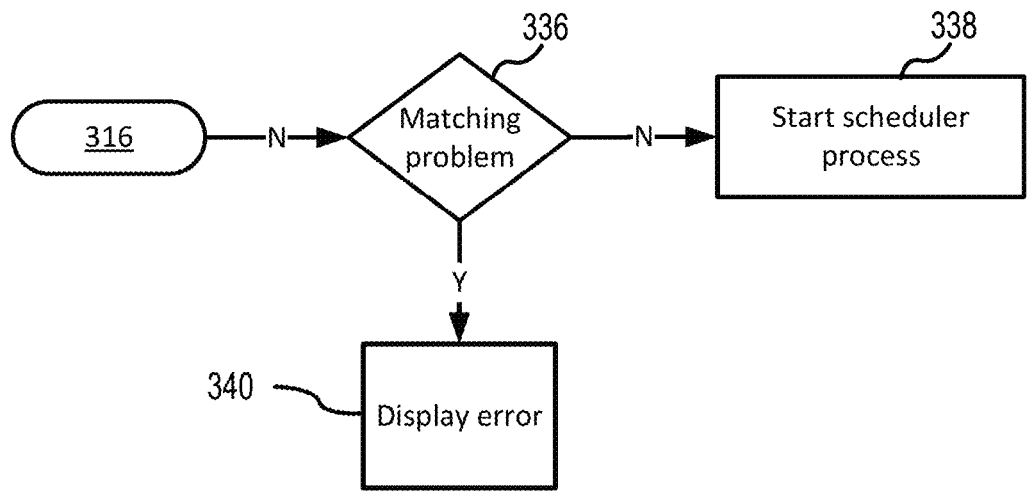
FIG. 3C illustrates a record matching fault process in an exemplary consumer health record access system in accordance with various embodiments.
Figure 4:
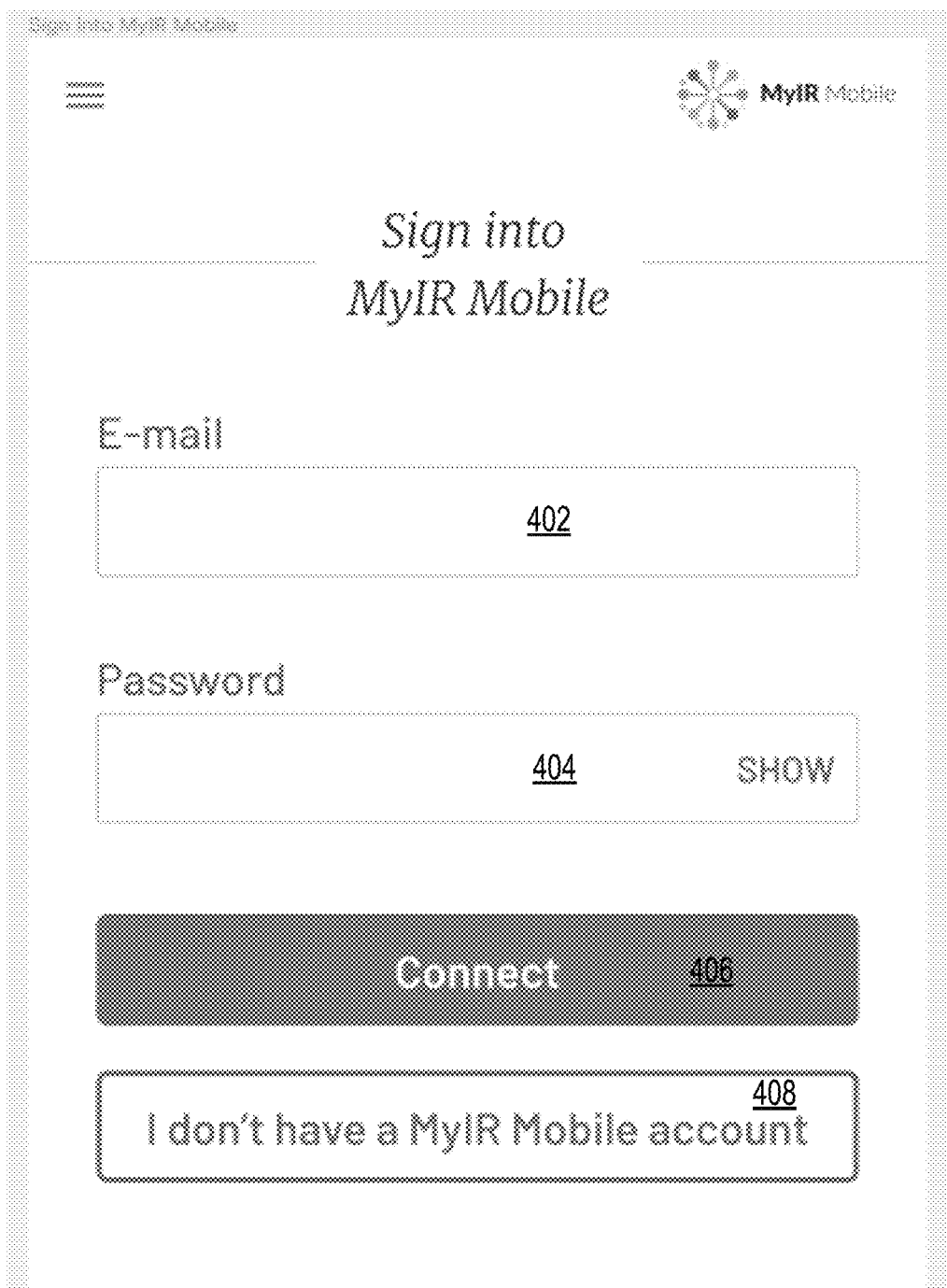
FIG. 4 illustrates a sign-in page of an exemplary consumer health record access system in accordance with various embodiments.
Figure 5:
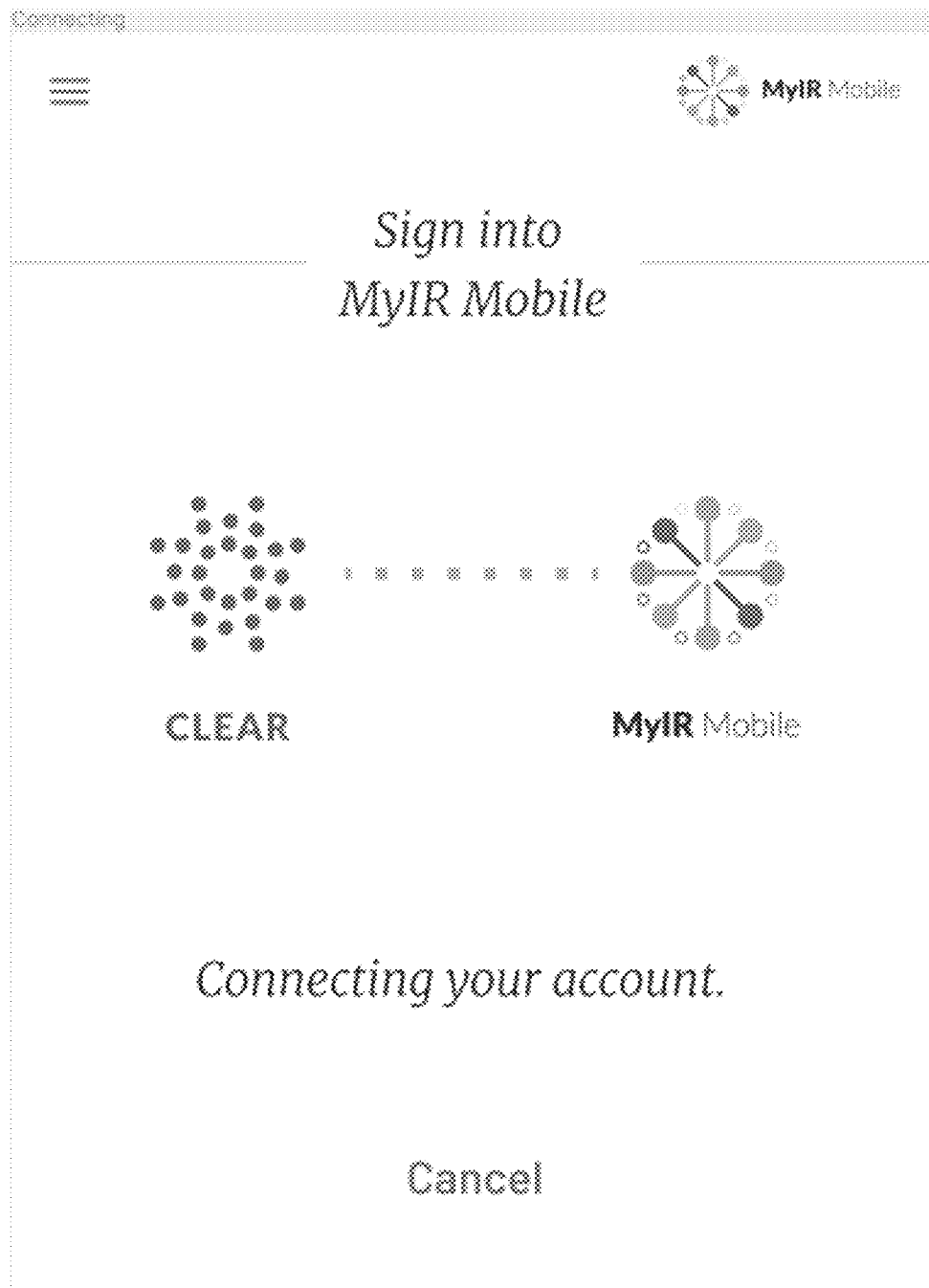
FIG. 5 illustrates a connecting account page of an exemplary consumer health record access system in accordance with various embodiments.

With additional reference to FIGS. 3A, 3B, and 3C, a process 300 for generating a passport report of system 115 is illustrated. The system may receive a request for a passport report and, in response, start process 300 (step 302). In various embodiments, the request for a passport report may be generated by a third party application. The system may receive authentication and/or sign-in information (step 304). For example, as shown in FIG. 4, the system may display a sign-in page 400 via the user device. Sign in page 400 may be configured to prompt a user to enter the sign-in information for a mobile device based application account. Page 400 may include one or more fields configured to receive text data. In various embodiments, the sign-in information may comprise an email address which may via an email field 402 and a password which may be received via password field 404. The system may perform and account check and determine whether an existing account associated with the sign-in information is configured in system 115 (step 306). For example, page 400 may display a connect button 406. The system may generate a connection event in response to a user interaction with the connect button 406. The system may perform the account check in response to generating the connection event.

Where no existing account is associated with the sign-in information, they system may start an account setup process 308. For example, page 400 may display an account creation button 408. The system may generate an account creation event in response to a user interaction with the account creation button 408. The system may start the account setup process 308 in response to the account creation event. In response to determining an existing account is associated with the sign-in information, the system may, the system may attempt to enable a connection between the system 215 and third party passport report data user (step 310). In various embodiments and with additional reference to FIG. 5, a connecting account page 500 of system 115 is illustrated. The system may display the connecting account page 500 in response to generating the connection event.

Figure 8:
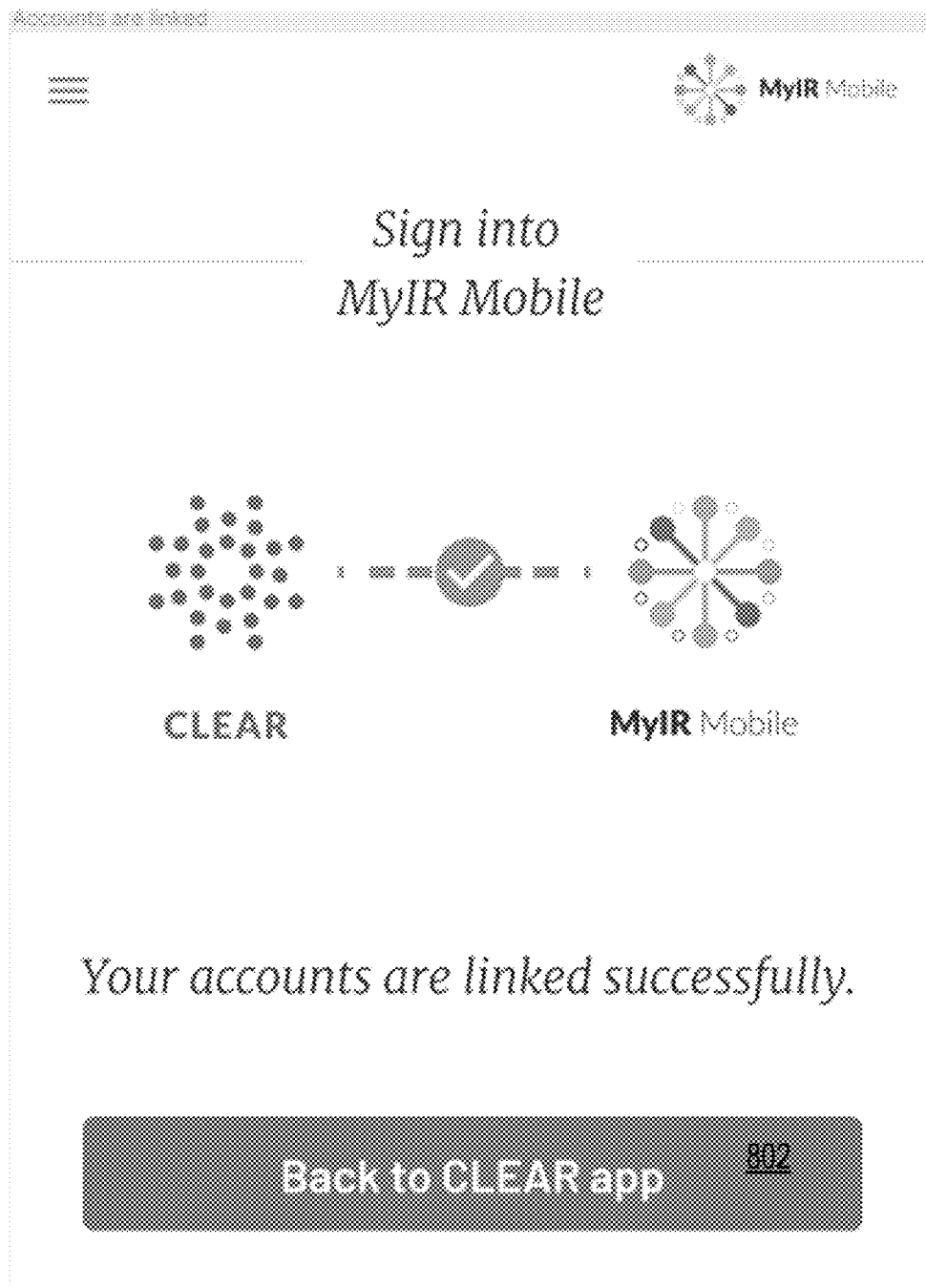
FIG. 8 illustrates a link successful page of an exemplary consumer health record access system in accordance with various embodiments.

In various embodiments, the system may determine whether the connection attempt is successful (step 312). If the connection attempt fails, the system may display a login error message 314. In various embodiments, error message 314 may comprise details about the nature of the connection attempt failure. In response to a successful connection attempt, the system may determine whether a desired set of records (e.g., consumer health record access database 250 records) are associated with the account (step 316). For example, the system may perform matching between the immunization and test records associated in database 250 with the account and a requirement set of immunization and test records. Where no records are found, the system may start a record matching fault process 318. Where records are found, the system may proceed to compile the passport report data based on the matching records (step 320). In various embodiments and with reference to FIG. 8, the system may display a link successful page 800 in response to compiling the passport report data. In various embodiments, the system may transmit the passport report data to the third party application and end process 300 (step 322). For example, page 800 may be configured to include a return button 802. The system may generate a return to third party application event in response to a user interaction with the return button 802. The system may transmit the passport report data to the third party application and may command the user device to return to the third party application in response to generating the return to third party application event.

In various embodiments and with renewed reference to FIG. 3B, account setup process 308 is illustrated. The system may receive personal information data (step 324). For example, the system may receive the personal information from a third party application or may receive personal information from the user device. The personal information may include a name, a gender, a date of birth, a phone number, an email address, a mailing address, a consent to release information, and/or the like. In various embodiments, the system may transmit a request for personal information to a third party application and may receive the personal information via the API of the passport module 249.

In various embodiments, the system may determine whether the personal information is correct (step 326). For example, as illustrated in FIG. 6, the system may display a confirmation page 600. The confirmation page 600 may display one or more elements of the personal information received in step 324 such as, for example, name, gender, date of birth, phone number, and mailing address. If the information is incorrect, they system may prompt to update the information and/or start an update profile process (step 328). For example, page 600 may display an update information button 604. The system may generate an update information event in response to a user interaction with the update information button (604). In response to generating the update information event, the system may start the update information process and thereby enable user editing of the personal information.

Figure 7:
FIG. 7 illustrates an account creation success page of an exemplary consumer health record access system in accordance with various embodiments.
Figure 9:
FIG. 9 illustrates a database targeting page of an exemplary consumer health record access system in accordance with various embodiments.

If the information is correct, the system may proceed to receive external health database targeting data (step 330). In various embodiments, as shown in FIG. 9, the system may display a database targeting page 900. The system may prompt to select one or more state immunization databases 260, lab provider systems 262, and/or healthcare provider systems 265. For example, page 900 may include a state database menu 902 and a healthcare provider menu 904. For example, user may interact with the menus 902, 904 and thereby the system may receive external heal database targeting data to configure data handler 244. Step 300 may include extracting and/or ingesting health records from the databases defined by the external health database targeting data. In response to receiving the health records, the system may generate a new account associated with the health records (step 332). The system may determine whether the new account was successfully generated and associated with the health records and proceed to step 316. In various embodiments, as shown in FIG. 7, the system may display an account creation success page 700 in response to successfully generating the new account. Otherwise, the system may generate an error message (step 334). The system may display the error message via the user device.

In various embodiments and with renewed reference to FIG. 3C, record matching fault process 318 is illustrated. The system may determine whether the health records match with the requirement set of immunization and test records, the personal information, and/or the like (step 336). For example, the system may perform key field matching between the health records set and the requirements set. Where a match is unable to be determined, the system may generate an error (step 340). In various embodiments, in response to determining the health records match with the requirement set, the system may determine an unmet requirement. In response to determining an unmet requirement, the system may start a scheduler process (step 338). For example, the requirement set may include a matching record showing immunization for measles. If no health record of measles immunization is found, the system may start the scheduler process to enable scheduling of a measles immunization by a consumer at a healthcare provider. In another example, the requirement set may include a matching lab report showing a negative test for an illness having been generated within the last 30 days. If no health record newer than 30 days old showing the negative test for an illness is found, the system may start the scheduler process to enable scheduling of the test by the consumer at a lab provider.

Figure 10:
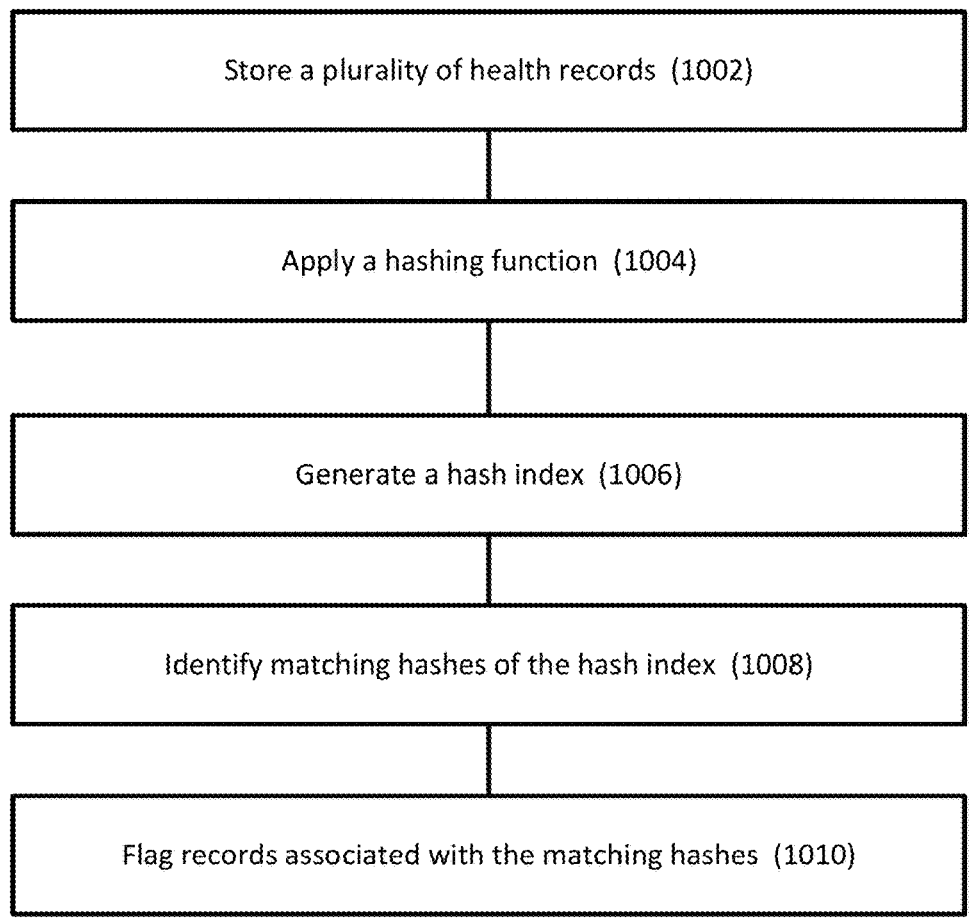
FIG. 10 illustrates an error detection process in an exemplary consumer health record access system in accordance with various embodiments.

In various embodiments and with reference to FIG. 10, an error detection process 1000 of the system 115 is illustrated. The system may store a plurality of health records in, for example, consumer health record access database 250 and/or primary database 150 (step 1002). The data processing module 252 may apply a hashing function to the plurality of records (step 1004). The data processing module 252 may generate, based on the hashing function, a hash index wherein each hash of the hash index is associated on a one-to-one basis with each record of the plurality of records (step 1006). The data processing module 252 may identify matching hashes within the hash index (step 1008). The data processing module 252 may flag the records associated with the matching hashes of the hash index for further processing (step 1010).

In various embodiments and with reference to FIG. 12, a machine learning based error correction process 1100 of the system 115 is illustrated. The system may store a similarity threshold value in the database 150 (step 1202). Step 1202 may include storing a dissimilarity threshold value in the database 150. Step 1202 may include store a training data set. The system may execute the data processing module 252 as configured to apply algorithmic transformations to the health records (step 1204). Step 1204 may include executing machine learning module 1100, self learning system 1102, training system 1104, and feedback system 1106. The system may automatically calculate a first set of weights associated with a first set of factors of a plurality of factors, stored in association with each health record of the training data set of health records (step 1206). The system may automatically enter the first set of weights and first set of associated factors into a similarity score model (step 1208). The system may execute the similarity score module 1112 to calculate a similarity score for each one of the plurality of health records associated with the respective customer account, wherein the respective similarity score for the respective health record is based on at least one weight of the first set of weights and at least one factor of the first set of factors of the similarity score model (step 1210). The system may compare the similarity score for each record with the similarity threshold value and the dissimilarity threshold value to determine a subset of the health records which exceed either value (step 1212). The system may flag health records as similar or as dissimilar based on the comparing of the similarity score (step 1214). The system may execute a corrective action only for those consumer accounts which have associated health records flagged as similar or dissimilar (step 1216).

Figure 13:
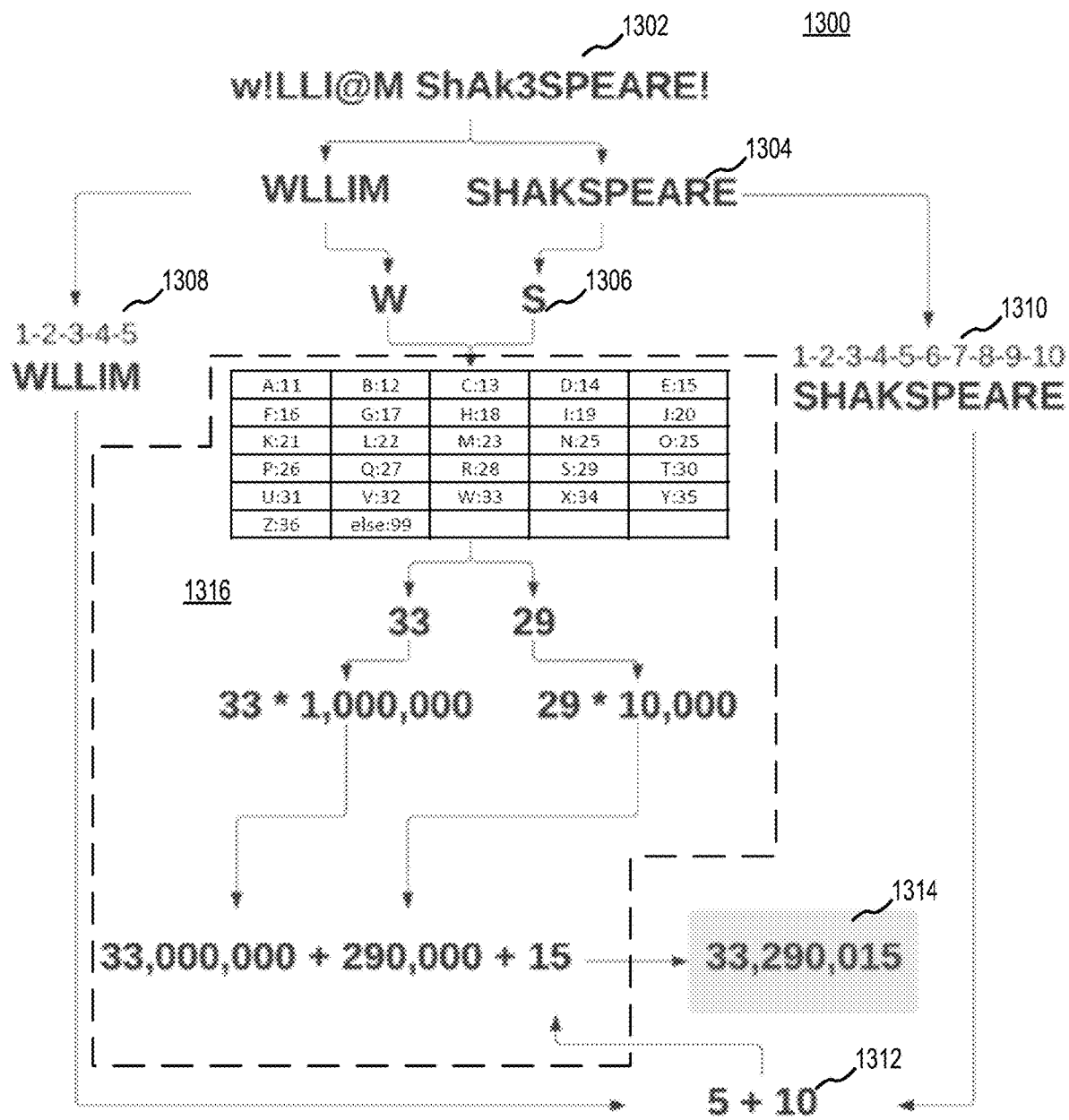
FIG. 13 illustrates a process flow of a hash function in an exemplary consumer health record access system in accordance with various embodiments.

With additional reference to FIG. 13, a process flow 1300 for a hash function 1316 is shown in accordance with various embodiments. A text string "w!LLI@M ShAk3SPEARE!" comprising a first name element and a last name element is input into the hash function at 1302 by the data processing module 252. In response to execution by the processor, the data processing module 252 pulls a text string from the database 250 and automatically enter the associated data elements into the hash function. The data processing module 252 separates the text string into the first name element and the last name element at 1304 and may remove non-letter characters (e.g., punctuation marks, numerals, and non-text symbols such as @, #, $, % and or the like). The data processing module 252 enters the first letter "W" of the first name element and the first letter "S" of the last name element into the hash function at 1308. The data processing module 252 counts the remaining letters of the first name element at 1308 and the remaining letters of the last name element at 1310. The counted values are entered into the hash function at 1312. In various embodiments, the sum of the first name element letter count and the last name element letter count may be entered into the hash function. The hash function performs the hashing operation on the text string based on the entered data elements and returns an eight digit integer at 1314.

While the present disclosure may be described in terms of a consumer, a healthcare provider, a state immunization registry, and so forth, one skilled in the art can appreciate that similar features and principles may be applied to other industries.

While the exemplary embodiments described herein are described in sufficient detail to enable those skilled in the art to practice principles of the present disclosure, it should be understood that other embodiments may be realized and that logical and/or functional changes may be made without departing from the spirit and scope of the present disclosure. Thus, the detailed description herein is presented for purposes of illustration and not of limitation.

While the description references specific technologies, system architectures and data management techniques, practitioners will appreciate that this description is of various embodiments, and that other devices and/or methods may be implemented without departing from the scope of principles of the present disclosure. Similarly, while the description references a user interfacing with the system via a computer user interface, practitioners will appreciate that other interfaces may include mobile devices, kiosks and handheld devices such as mobile phones, smart phones, tablet computing devices, etc.

While the steps outlined herein represent exemplary embodiments of principles of the present disclosure, practitioners will appreciate that there are any number of computing algorithms and user interfaces that may be applied to create similar results. The steps are presented for the sake of explanation only and are not intended to limit the scope of the present disclosure in any way. Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all of the claims.

It should be understood that the detailed description and specific examples, indicating exemplary embodiments, are given for purposes of illustration only and not as limitations. Many changes and modifications may be made without departing from the spirit thereof, and principles of the present disclosure include all such modifications. Corresponding structures, materials, acts, and equivalents of all elements are intended to include any structure, material, or acts for performing the functions in combination with other elements. Reference to an element in the singular is not intended to mean "one and only one" unless explicitly so stated, but rather "one or more." Moreover, when a phrase similar to "at least one of A, B, or C" or "at least one of A, B, and C" is used in the claims or the specification, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

The systems and methods herein may be described in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, Java, JavaScript, Flash, ActionScript, FLEX, VBScript, Macromedia Cold Fusion, COBOL, Microsoft Active Server Pages, assembly, PERL, SAS, PHP, awk, Python, Visual Basic, SQL Stored Procedures, PL/SQL, any UNIX shell script, extensible markup language (XML), and/or the like, with the various algorithms being implemented with any combination of data structures, objects, processes, routines or other programming elements. Further, it should be noted that the system may employ any number of conventional techniques for data transmission, signaling, data processing, network control, and the like. Still further, the system may be used to detect or prevent security issues with a client-side scripting language, such as JavaScript, VBScript and/or the like.

Software elements may be loaded onto a general purpose computer, special purpose computer, or other programmable data processing apparatus to produce a machine, such that the instructions that execute on the computer or other programmable data processing means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified herein or in flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, web pages, web sites, web forms, prompts, etc. Practitioners will appreciate that the illustrated steps described herein may comprise any number of configurations including the use of windows, web pages, web forms, popup windows, prompts and/or the like. It should be further appreciated that the multiple steps as illustrated and described may be combined into single web pages and/or windows but have been expanded for the sake of simplicity. In other cases, steps illustrated and described as single process steps may be separated into multiple web pages and/or windows but have been combined for simplicity.

What is claimed is:

1. A consumer health records access platform including a software application for operation on a user device, the system comprising:

a processor;

a tangible, non-transitory electronic memory in electronic communication with the processor, a set of computer readable code on the non-transitory electronic memory, including:

a consumer module configured for use by consumers to support registering consumers for a consumer account pending authentication and approval by a healthcare provider;

a provider module configured to enable, via a healthcare provider account, the healthcare provider to look up the consumer account pending authentication and to authenticate and approve or reject creation of the consumer account;

a recording agency module configured for use by recording agency representatives to create, via a recording agency account, the healthcare provider account;

a consumer health record access database comprising a plurality health records associated on a many to one basis with each of a plurality of consumer accounts;

a training data set of health records;

a plurality of factors stored in association with each health record associated with a respective consumer account;

a data processing module, executable by the processor, configured to apply algorithmic transformations to the plurality of health records and comprising a machine learning module including a self learning system, a training system, and a feedback system, wherein, in response to execution by the processor, the self learning system automatically calculates a first set of weights associated with a first set of factors of a plurality of factors stored in association with each health record of the training data set of health records, and enters the first set of weights and first set of associated factors into a similarity score model;

a similarity threshold value;

a dissimilarity threshold value;

a factor entering module, executable by the processor, to enter at least one factor from the plurality of factors stored in association with each health record associated with the respective consumer account into a similarity score module, wherein the similarity score module is executable by the processor to calculate a similarity score for each one of the plurality of health records associated with the respective customer account, wherein a respective similarity score for the each one of the plurality of health records is based on at least one weight of the first set of weights and at least one factor of the first set of factors of the similarity score model;

a comparator that is executable by the processor to compare the similarity score for each record with the similarity threshold value and the dissimilarity threshold value to determine a subset of the plurality of health records that exceed either value, wherein the comparator allows for comparing the similarity score for each health record of a set of incoming health records received via bi-directional HL7 messaging from each of the healthcare provider and a state immunization registry to the similarity score for each of the plurality of health records of the consumer health record access database;

a flagging unit that is executable by the processor to flag health records of the plurality of health records as similar or as dissimilar based on an output of the comparator; and a corrective action module that is executable by the processor to perform a corrective action only for those consumer accounts which have associated health records flagged by the flagging unit.

2. The consumer health records access platform of claim 1, wherein the feedback system is executable by the processor, to automatically update the at least one weight of the first set of weights associated with the first set of factors of the plurality of factors stored in association with each health record of the training data set of health records based on information received by the feedback system, wherein the self learning system is executable to generate a second set of weights including the updated weight for entry into the similarity score model, wherein the similarity score module calculates a different similarity score for a selected heath record before the feedback system is executed than after.

3. The consumer health records access platform of claim 1, wherein the feedback system is executable by the processor to automatically remove the at least one factor of the first set of factors in response to information received by the feedback system.

4. The consumer health records access platform of claim 2, wherein the feedback system is executable by the processor to automatically add one or more factors to the first set of factors in response to information received by the feedback system, wherein the self learning system is executable to generate a second set of factors including the one or more factors for entry into the similarity score model.

5. The consumer health records access platform of claim 3, wherein the at least one factor entered into the similarity score model is a first name.

6. The consumer health records access platform of claim 2, wherein the at least one factor entered into the similarity score model is a last name.

7. The consumer health records access platform of claim 3, wherein the at least one factor entered into the similarity score model is a date of birth.

8. The consumer health records access platform of claim 3, wherein the at least one factor entered into the similarity score model is a social security number.

9. The consumer health records access platform of claim 3, wherein the at least one factor entered into the similarity score model is a year of birth.

10. The consumer health records access platform of claim 3, wherein the at least one factor entered into the similarity score model is a gender.

11. The consumer health records access platform of claim 3, wherein the at least one factor entered into the similarity score model is a birth order.

12. The consumer health records access platform of claim 3, wherein the at least one factor entered into the similarity score model is a street address.

13. The consumer health records access platform of claim 3, wherein the at least one factor entered into the similarity score model is a zip code.

14. The consumer health records access platform of claim 3, wherein the at least one factor entered into the similarity score model is an output of a hash function.

15. The consumer health records access platform of claim 14, wherein the hash function is based on record elements comprising at least one of a first name, a last name, a date of birth, a first name character length, a last name character length, a combined first and last name character length, a date of birth year, a first name initial, or a last name initial.

16. The consumer health records access platform of claim 15, wherein the hash function returns an eight digit integer.

17. The consumer health records access platform of claim 1, wherein the corrective action module allows for:

in response to receiving user input identifying flagged health records as similar, entering information into the feedback system confirming the flagged health records as similar, and responsively merging the flagged health records.

18. The consumer health records access platform of claim 1, wherein the corrective action module allows for:

in response to receiving user input identifying flagged health records as dissimilar health records, entering information into the feedback system confirming the dissimilar health records as dissimilar, and responsively storing the dissimilar health records in the consumer health record access database as new health records.

19. A method comprising:

storing, by a processor, a plurality health records associated on a many to one basis with each of a plurality of consumer accounts;

storing, by the processor, a similarity threshold value;

storing, by the processor, a dissimilarity threshold value;

storing, by the processor, training data set of health records;

executing, by the processor, a data processing module configured to apply algorithmic transformations to the plurality of health records and comprising a machine learning module including a self learning system, a training system, and a feedback system;

automatically calculating, by the processor, a first set of weights associated with a first set of factors of a plurality of factors, stored in association with each health record of the training data set of health records;

automatically entering, by the processor, enters the first set of weights and first set of associated factors into a similarity score model;

entering, by the processor, at least one factor from the plurality of factors stored in association with each health record associated with a respective consumer account into a similarity score module;

executing, by the processor, the similarity score module to calculate a similarity score for each one of the plurality of health records associated with the respective customer account, wherein a respective similarity score for the each one of the plurality of health records is based on at least one weight of the first set of weights and at least one factor of the first set of factors of the similarity score model;

comparing, by the processor, the similarity score for each record with the similarity threshold value and the dissimilarity threshold value to determine a subset of the plurality of health records which exceed either value;

comparing, by the processor, the similarity score for each health record of a set of incoming health records received via bi-directional HL7 messaging from each of the healthcare provider and a state immunization registry to the similarity score for each of the plurality of health records of the consumer health record access database flagging, by the processor, health records of the plurality of health records as similar or as dissimilar based on the comparing of the similarity score; and executing, by the processor, a corrective action only for those consumer accounts or records which have associated health records flagged as similar or dissimilar.

20. The method of claim 19, further comprising:

receiving, by the processor, feedback information from the feedback system;

automatically updating, by the processor, the at least one weight of the first set of weights associated with the first set of factors of the plurality of factors stored in association with each health record of the training data set of health records based on the feedback information received by the feedback system; and executing, by the processor, the self learning system to generate a second set of weights including the updated weight for entry into the similarity score model, wherein the similarity score module calculates a different similarity score for a selected heath record before the updating than after.

21. The method of claim 19, further comprising removing, by the processor, the at least one factor of the first set of factors in response to feedback information received by the feedback system.

22. The method of claim 20, further comprising adding one or more factors to the first set of factors in response to the feedback information received by the feedback system, wherein the self learning system is executable to generate a second set of factors including the one or more factors for entry into the similarity score model.

23. An article of manufacture including a non-transitory, tangible computer readable storage medium having instructions stored thereon that, in response to execution by a processor, cause the processor to perform operations comprising:

storing, by the processor, a plurality health records associated on a many to one basis with each of a plurality of consumer accounts;

storing, by the processor, a similarity threshold value;

storing, by the processor, a dissimilarity threshold value;

storing, by the processor, training data set of health records;

executing, by the processor, a data processing module configured to apply algorithmic transformations to the plurality of health records and comprising a machine learning module including a self learning system, a training system, and a feedback system;

automatically calculating, by the processor, a first set of weights associated with a first set of factors of a plurality of factors, stored in association with each health record of the training data set of health records;

automatically entering, by the processor, enters the first set of weights and first set of associated factors into a similarity score model;

entering, by the processor, at least one factor from the plurality of factors stored in association with each health record associated with a respective consumer account into a similarity score module;

executing, by the processor, the similarity score module to calculate a similarity score for each one of the plurality of health records associated with the respective customer account, wherein a respective similarity score for the each one of the plurality of health records is based on at least one weight of the first set of weights and at least one factor of the first set of factors of the similarity score model;

comparing, by the processor, the similarity score for each record with the similarity threshold value and the dissimilarity threshold value to determine a subset of the plurality of health records which exceed either value;

comparing, by the processor, the similarity score for each health record of a set of incoming health records received via bi-directional HL7 messaging from each of the healthcare provider and a state immunization registry to the similarity score for each of the plurality of health records of the consumer health record access database flagging, by the processor, health records of the plurality of health records as similar or as dissimilar based on the comparing of the similarity score; and executing, by the processor, a corrective action only for those consumer accounts which have associated health records flagged as similar or dissimilar.

24. The article of manufacture of claim 23, wherein the operations further comprise:

receiving, by the processor, feedback information from the feedback system;

automatically updating, by the processor, the at least one weight of the first set of weights associated with the first set of factors of the plurality of factors stored in association with each health record of the training data set of health records based on the feedback information received by the feedback system; and executing, by the processor, the self learning system to generate a second set of weights including the updated weight for entry into the similarity score model, wherein the similarity score module calculates a different similarity score for a selected heath record before the updating than after.

25. The article of manufacture of claim 23, wherein the operations further comprise removing, by the processor, the at least one factor of the first set of factors in response to feedback information received by the feedback system.

26. The article of manufacture of claim 24, wherein the operations further comprise adding one or more factors to the first set of factors in response to the feedback information received by the feedback system, wherein the self learning system is executable to generate a second set of factors including the one or more factors for entry into the similarity score model.

27. The article of manufacture of claim 23, wherein the at least one factor entered into the similarity score model is a first name, a last name, a date of birth, a first name character length, a last name character length, a combined first and last name character length, a date of birth year, a first name initial, or a last name initial.

* * * * *